United States Patent [19]
Kanojia et al.

[11] Patent Number: 4,775,757
[45] Date of Patent: Oct. 4, 1988

[54] THIENOPYRIDINES USEFUL AS CARDIOVASCULAR AGENTS

[75] Inventors: Ramesh M. Kanojia, Somerville; James J. McNally, High Bridge; Jeffery B. Press, Rocky Hill, all of N.J.

[73] Assignee: Ortho Pharmaceutical Corporation, Raritan, N.J.

[21] Appl. No.: 909,817

[22] Filed: Sep. 22, 1986

[51] Int. Cl.$^4$ ............... C07D 401/14; C07D 495/02
[52] U.S. Cl. ............................. 544/362; 546/114
[58] Field of Search .............. 544/362; 546/114; 514/253, 301

[56] References Cited

U.S. PATENT DOCUMENTS

| | | | |
|---|---|---|---|
| 4,104,390 | 8/1978 | Ferrand et al. | 514/301 |
| 4,136,186 | 1/1979 | Frehel et al. | 514/301 |
| 4,147,787 | 4/1979 | Maffrand | 514/301 |
| 4,165,374 | 8/1979 | Troxler et al. | 514/301 |
| 4,496,568 | 1/1985 | Maffrand | 546/114 |
| 4,550,106 | 10/1985 | Schneider et al. | 514/301 |

Primary Examiner—Donald G. Daus
Assistant Examiner—Cecilia Shen
Attorney, Agent, or Firm—Benjamin F. Lambert

[57] ABSTRACT

The synthesis of thienopyridine derivatives is described. The novel thienopyridine derivatives are cardiotonic agents and renal vasodilating agents. The compounds are useful as cardiovascular agents.

9 Claims, No Drawings

THIENOPYRIDINES USEFUL AS CARDIOVASCULAR AGENTS

BACKGROUND OF THE INVENTION

1. Field of the Invention

The present invention relates to novel thienopyridine derivatives of general formula I:

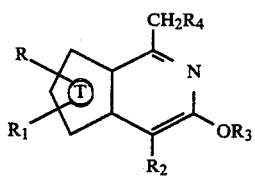

as described further below. The derivatives are useful as cardiovascular agents such as cardiotonic agents or renal vasodilating agents.

2. Description of the Prior Art

Any drug that affects the heart or blood vessels, directly or indirectly, is a cardiovascular drug, although the term generally connotes only those drugs which are used for their cardiovascular actions. Many such drugs exist. Nearly every autonomic drug has clinically applicable cardiovascular actions. Sympathomimetics may be used to elevate blood pressure, stimulate the heart, slow the heart reflexly, etc., depending on the particular agents and the clinical conditions. Adrenergic blocking drugs may be used in vasopastic conditions, in the diagnosis and management of pheochromocytoma, and rarely in malignant and toxemic hypertensive crises. Cholinomimetic drugs may be used as vasodilators, and under unusual conditions as cardiodecelerators in atrial tachycardia, although their usual action is to speed the heart reflexly. Atropine and other antimuscarinic drugs may be used to block the cardiac vagus nerve in Adams-Stokes syndrome and certain other bradycardias. The ganglionic blocking agents may be used to lower the blood pressure and increase the peripheral blood flow. Most of the antihypertensive agents can be considered autonomic drugs. Among the antihypertensive agents are compounds which are within the kidney to produce renal vasodilation. Selective renal vasodilation may result in increased renal perfusion with concommitant improved renal efficiency and reduction in elevated blood pressure. Guyton, T. G., et al., *Circ. Res.* 35, 159 (1974). Renal vasodilators can be identified by the procedure of Goldberg, L. I., et al., *J. Pharmacol. Exp. Ther.* 163, 188 (1968).

Compounds that stimulate myocardial contractility may be useful in the treatment of heart failure. Bristol, J. A., et al., *Med. Res. Rev.* 3, 259 (1983). Such compounds are called cardiotonics or positive inotropic agents. Cardiotonics increase the strength of contraction of the heart muscle and increase cardiac tone. The improved coronary blood supply which comes in the wake of a compensated circulation improves the nutrition and strength of the heart. Slowing of the cardiac rate occurs only when the rate was originally rapid due to the failure. When the failure is abolished, there is no longer any need for the compensatory tachycardia, and consequently the heart rate slows to normal. The most widely known cardiotonics are digitalis and its allied cardiac glycosides. Positive inotropic agents can be identified by an in vivo evaluation of cardiac force, dP/dt maximum, heart rate and mean arterial blood pressure after administration of the drug. Alousi, A. A., et al., *J. Circ. Res.* 45, 666 (1979).

SUMMARY OF THE INVENTION

The present invention is directed to thienopyridine compounds of the formula

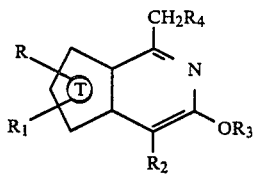

where

may be

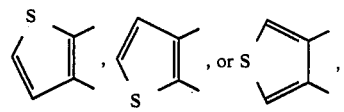

R and $R_1$ may be the same or different and may be hydrogen or methyl;

$R_2$ may be hydrogen, Cl, Br, I, $NO_2$, $NH_2$, $C_1$-$C_6$ alkyl, —$CO_2R_5$, —$NHCONHR_6$, —$NHCO_2R_5$ or —NHCOR_7$;

$R_3$ may be hydrogen, $COR_8$ or —$(CH_2)_nN(CH_3)_2$;

$R_4$ may be hydrogen, Br, —$N(R_5)_2$ or

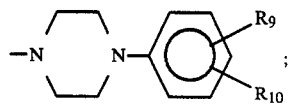

$R_5$ may be $C_1$-$C_3$ alkyl;

$R_6$ may be hydrogen, $C_1$-$C_6$ alkyl or

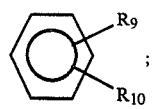

$R_7$ may be $C_1$-$C_6$ alkyl or

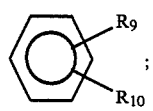

$R_8$ may be $C_1$-$C_4$ alkyl or

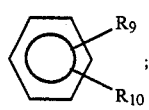

$R_9$ and $R_{10}$ may be the same or different and may be hydrogen, $C_1$-$C_3$ alkyl, —COOH, —CH$_3$, —OCH$_3$ or halogen; and n may be 2–5; provided that $R_2$ is not hydrogen when R and $R_1$ are methyl.

The compounds of formula I are useful as cardiovascular agents, such as cardiotonic agents or renal vasodilating agents.

DETAILED DESCRIPTION OF THE INVENTION

The invention in its broadest aspects relates to thienopyridine compounds which have cardiovascular activity, such as cardiotonic activity or renal vasodilating activity, in mammals. The thienopyridine compounds of the invention demonstrating a cardiovascular activity are shown by formula I above. The thienopyridine component of formula I may be either thieno[2,3-c]pyridine, thieno[3,2-c]pyridine or thieno[3,4-c]pyridine.

The preferred compounds of the present invention are those wherein R is hydrogen or methyl, $R_1$ is hydrogen, $R_2$ is hydrogen, Br, Cl, NO$_2$, NH$_2$,

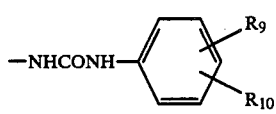

alkyl, —CO$_2$(C$_1$-C$_3$ alkyl), —NHCONH$_2$, or NHCO(C$_1$-C$_6$ alkyl), $R_3$ is hydrogen, —(CH$_2$)$_n$N(CH$_3$)$_2$ or —COC$_1$-C$_4$ alkyl), and $R_4$ is hydrogen, Br, or

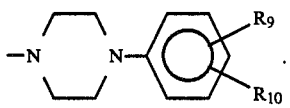

The thieno[2,3-c]pyridine compounds of formula I can be prepared as shown in Scheme 1:

Scheme 1

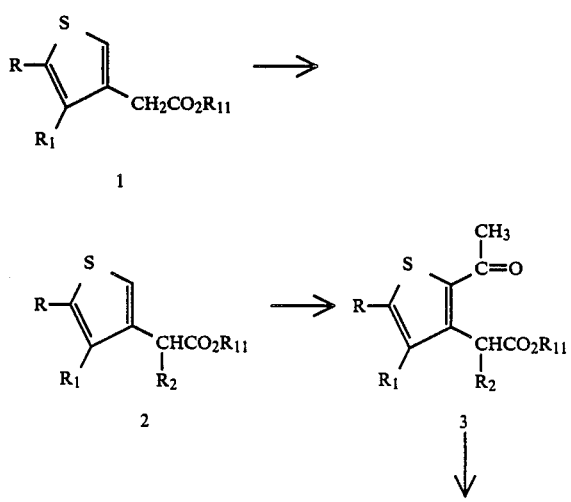

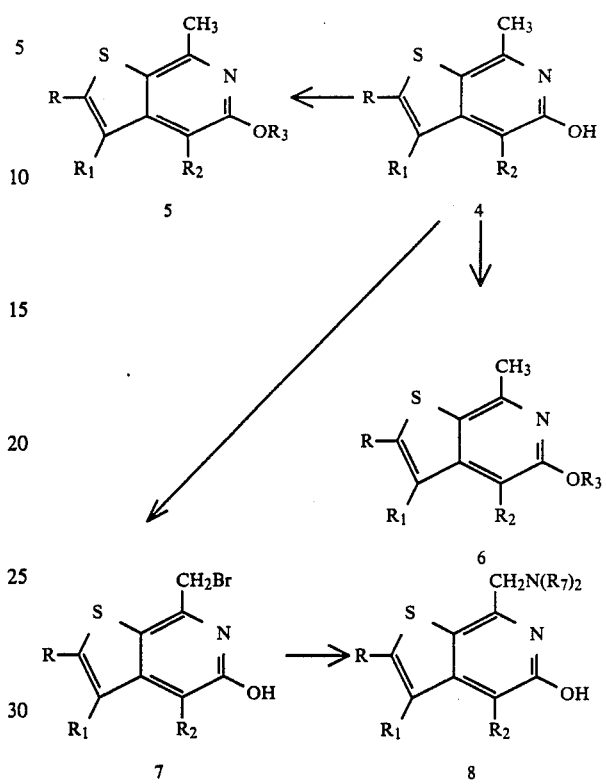

The thieno[2,3-c]pyridine compounds of formula I are prepared as follows:

3-Thiopheneacetic acid methylester 1 ($R_{11}$=CH$_3$) is acetylated with acetic anhydride and a perchloric acid catalyst at about $-20°$ to 20° C. for about 0.5–2 hours to produce the acetyl derivative 3 where $R_2$ is hydrogen. Alternatively, the 3-thiophenacetic acid methyl ester 1 is reacted with a strong base in an inert solvent at about $-78°$ to $-60°$ C. for about 0.5–1 hour. A preferred strong base is lithium diisopropylamide. A preferred inert solvent is tetrahydrofuran. The product is subsequently reacted with either an alkyl halide or an acylating agent in the inert solvent at the same temperature for about 0.5–2 hours to produce the substituted ester 2. The ester 2 is acetylated as described above to produce the acetyl derivative 3. The acetyl derivative 3 is reacted with ammonia in molten ammonium acetate to produce the thieno[2,3-c]pyridine 4.

When $R_2$ is H in the thieno[2,3-c]pyridine 4, reaction with electrophilic reagents produces the derivatives in good yields. Thus, reaction with bromine, for example, provides the bromo derivative 4 ($R_2$=Br) while sulfuryl chloride provides the chloro derivative 4 ($R_2$=Cl), and nitric acid yields the nitro derivative 4 ($R_2$=NO$_2$), all as solids. The nitro derivative is hydrogenated using 10% palladium on carbon catalyst to produce the amine derivative. This amine is reacted with various acylating agents such as acetic anhydride to give the amide derivative 4 ($R_2$=NHCO$_3$R$_7$), sodium cyanate to give unsubstituted area 4 ($R_2$=NHCONH$_2$) or with alkyl isocyanates such as butyl isocyanate or with aryl isocyanates such as 2-methoxyphenylisocyanate to give substituted ureas 4 ($R_2$=NHCONHC$_4$H$_9$) or 6 (X=NHCONH-Ph-2-OCH$_3$) respectively. Treatment of 4 with acetic anhydride with sulfuric acid catalyst produces the compounds 5 ($R_3$=OCOCH$_3$) or 6 ($R_3$=OCOCH$_3$), respectively. If 4 is treated with a strong base such as sodium hydride and subsequently reacted with an alkylating agent such as dimethylaminoethyl chloride or dimethylaminopropyl chloride, the compounds 5 or 6 where $R_3$=(CH$_2$)$_2$N(CH$_3$)$_2$ or $R_3$=(CH$_2$)$_3$N(CH$_3$)$_2$ are formed, respectively.

Reaction of 4 ($R_2$=H) with two equivalents of bromine yields the dibromide 7 ($R_2$=Br). Similarly, bromination of 4 when $R_2$ is other than hydrogen with one equivalent of bromine produces bromide 7. Reaction of 7 with amines such as HN($R_7$)$_2$ yields 8.

The thieno[3,2-c]pyridine compounds of formula I can be prepared as shown in Scheme 2.

Scheme 2

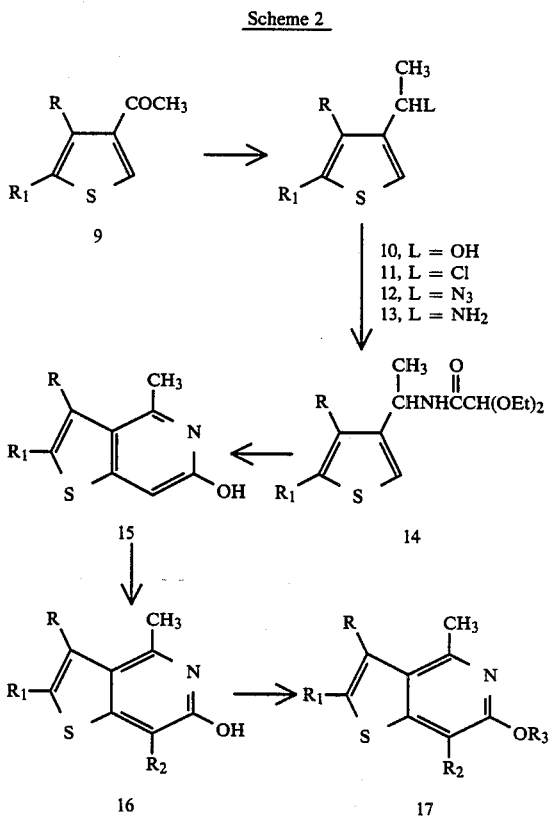

The thieno[3,2-c]pyridine compounds of formula I are prepared as follows: 3-Acetylthiophene 9 is reacted with a metal hydride reducing agent, such as lithium aluminum hydride, in an inert solvent, such as ether, to reflux temperatures for about 0.5-6 hours to produce the alcohol 10 as an oil. Reaction of 10 with thionyl chloride at 0° C. for about 1-5 hours yields the chloride 11 as an oil. Conversion of 11 to the azide 12 is accomplished by reaction with sodium azide in a polar solvent, such as dimethylformamide, for about 1-3 days; 12 was reduced by a metal hydride reducing agent, such as lithium aluminum hydride, to give the amine 13 as an oil. Amine 13 is reacted with ethyl diethoxyacetate in an inert solvent, such as methylene chloride, in the presence of trimethylaluminum at reflux temperatures for about 1-6 hours to prepare the amide 14 as an oil. Alternatively, the chloride 11 is reacted with the anion of diethoxyacetamide (prepared by the action of a strong base, such as sodium hydride, in an inert solvent, such as tetrahydrofuran), catalyzed by sodium iodide at reflux temperatures for about 12-48 hours to yield the amide 14. The amide 14 is reacted in 47% hydrobromic acid in a protic solvent, such as acetic acid, at reflux temperatures for about 0.25-1 hour to give thieno[3,2-c]-pyridinol 15 as a solid.

Reaction of 15 with electrophilic reagents such as bromine or nitric acid in a polar solvent, such as acetic acid, yields the derivative 16 ($R_2$=Br or $R_2$=NO$_2$), respectively. Nitro compound 16 ($R_2$=NO$_2$) is reduced with hydrogen using 10% palladium on carbon catalyst to give the amine 16 ($R_2$=NH$_2$). The amine is reacted with various acylating agents, such as acetic anhydride, sodium cyanate, alkyl isocyanates or aryl isocyanates, to produce amide 16 ($R_2$=NHCOCH$_3$), urea 16 ($R_2$=NHCONH$_2$), or substituted urea 16 ($R_2$=NHCONHR$_6$), respectively. Treatment of 16 with acylating agents, such as acetic anhydride, or carboxylic acid halides, such as benzoyl chloride or optionally substituted benzoyl chloride, produce the derivatives 17 ($R_3$=COCH$_3$) or 17 ($R_3$=COAr), respectively.

The thieno[3,4-c]pyridine compounds of formula I can be prepared as shown in Scheme 3:

Scheme 3

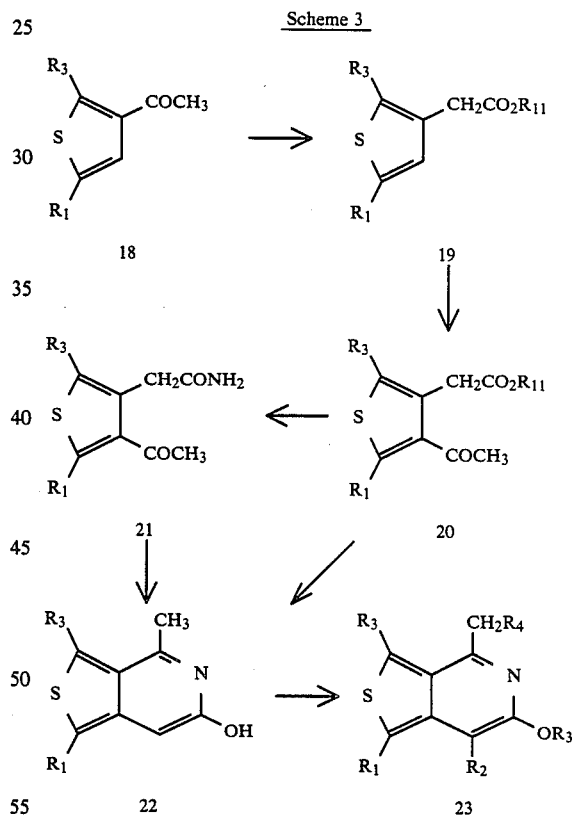

The thieno[3,4-c]pyridine compounds of formula I are prepared as follows: 3-Acetylthiopene 18 is reacted with sulfur in morpholine at reflux temperatures, and the resultant product is hydrolyzed in aqueous sodium hydroxide to give acid 19 ($R_{12}$=H) as a solid. Esterification in an alcoholic solvent, such as methanol or ethanol, using sulfuric acid catalysis yields the ester 19 ($R_{11}$=CH$_3$ or C$_2$H$_5$). Ester 19 is acetylated with acetyl chloride using a metal halide catalyst, such as tin tetrachloride, to give 20. Reaction of 20 with concentrated ammonium hydroxide produces a mixture of amide 21 and thienopyridinol 22. Ring closure of 21 is effected by dissolution in trifluoroacetic acid to give 22; alternatively, the mixture of 21 and 22 obtained from the ammonolysis could be converted to 22 directly by the action of trifluoroacetic acid. Compound 23, wherein $R_2$, $R_3$ and $R_4$ are as previously described, can be prepared as previously described in Schemes 1 and 2.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain unit dosage, e.g., tablet, capsule, powder, injection, teaspoonful and the like, from about 0.05 to about 50 mg/kg, and preferably from about 0.1 to about 10 mg/kg of the active ingredient.

The following examples describe the invention in greater particularity and are intended to be a way of illustrating but not limiting the invention.

EXAMPLE 1

Methyl 2-acetyl-3-thiophene acetate

Acetic anhydride (13.0 ml, 0.147 mol) was added dropwise to a mixture of 70% perchloric acid (1.25 g, 8.7 mmol) and methyl 3-thiophene acetate (19.15 g, 0.123 mol) at 0° C., and stirred at 0° C. for one hour. The reaction mixture was treated with 5% aqueous NaHCO$_3$ (100 ml). The product was extracted into CH$_2$Cl$_2$ (2×100 ml), the extract dried over MgSO$_4$ and purified by flash chromatography on silica gel 60 (450 g) eluted with 15% EtOAc in hexanes to give the product as a solid (10.4 g, 43% yield); mp 53°–54° C.; IR (KBr) 1735 and 1655 cm$^{-1}$; mass spectrum m/z 198 (M+); $^1$H NMR (CDCl$_3$) δ2.53 (s, 3H, COCH$_3$), 3.70 (s, 3H, CO$_2$CH$_3$), 4.05 (s, 2H, CH$_2$CO$_2$), 7.02 and 7.42 each (d, J=5 Hz, 1H, thiophene-$\underline{H}$).

Theor. C$_9$H$_{10}$O$_3$S: C, 54.52; H, 5.08. Found: C, 54.63; H, 5.06.

7-Methylthieno[2,3-c]pyridin-5-ol

Methyl 2-acetyl-3-thiophene acetate (3.65 g, 18.4 mmol) was added to molten ammonium acetate (46 g) at 130° C. Anhydrous ammonia was bubbled into the reaction mixture, maintained at 130° C. for 30 minutes. The hot mixture was poured into ice water (250 ml) and the pale green precipitate was collected by filtration and washed with water. The solid was recrystallized from isopropanol to give the product (1.89 g, 62% yield) as a pale green solid; mp 230°–231° C. (dec); IR (KBr) 2638, 1645, 1490 and 1455 cm$^{-1}$; $^1$H NMR (DMSO-d$_6$) δ2.52 (s, 3H, 7-CH$_3$), 6.70 (s, 1H, 4-$\underline{H}$), 7.21 (d, J=5 Hz, 1H, thiophene-$\underline{H}$), 7.87 (d, J=5 Hz, 1H, thiophene-$\underline{H}$); mass spectrum m/z 165 (M+).

Theor. C$_9$H$_{10}$NOS: C, 58.16; H, 4.27; N, 8.48; S, 19.41. Found: C, 57.92; H, 4.26; N, 8.36; S, 19.18.

When, in the above procedure, methyl 5-methyl-3-thiophene acetate, methyl 4-methyl-3-thiophene acetate or methyl 4,5-dimethyl-3-thiophene acetate is employed, the corresponding 2,7-dimethyl, 3,7-dimethyl, or 2,3,7-trimethyl derivative is obtained.

EXAMPLE 2

Methyl 2-(thien-3-yl)butanoate n-Butyllithium (1.6M, in hexane, 21 ml, 33.6 mmol) was added to a solution of diisopropylamine (5.0 ml, 36.2 mmol) in THF (40 ml) at $-10°$ C. under N$_2$ and stirred for 30 minutes. The solution was cooled to $-78°$ C., and at this temperature a solution of methyl-3-thiophene acetate (5.14 g, 32.9 mmol) in THF (10 ml) was added slowly. A yellow precipitate formed. The mixture was stirred at $-78°$ C. for one hour. Ethyl iodide (3.0 ml, 37.5 mmol) was added, and the mixture was stirred at $-78°$ C. for an additional 0.5 hour. The mixture was allowed to warm to room temperature over about 0.5 hour, during which time it became a clear solution. After stirring for one hour at room temperature, the mixture was poured into CH$_2$Cl$_2$ (300 ml) containing 1–3 g of ice. The separated organic layer was washed with 1N HCl (1×200 ml), dried over MgSO$_4$ and evaporated in vacuo to yield 5.6 g of a yellow oil. The oil was purified by flash chromatography on silica gel 60 (100 g) using ethyl acetate/hexanes (3:97) to give the product (4.62 g, 76% yield) as a colorless oil; IR (neat) 2958, 1736 cm$^{-1}$; mass spectrum m/z 184 (M+); $^1$H NMR (CDCl$_3$) δ0.90 (t, J=8 Hz, 3H, CH$_2$C$\underline{H}$$_3$), 1.65–2.23 (m, 2H, C$\underline{H}$$_2$CH$_3$), 3.59 (t, J=7.5 Hz, 1H, C$\underline{H}$CH$_2$), 3.65 (s, 3H, CO$_2$C$\underline{H}$$_3$), 6.90–7.28 (m, 3H, thiophene-$\underline{H}$), UV (EtOH): 236 (ε=51848).

Theor. C$_9$H$_{12}$OS: C, 58.67; H, 6.56. Found: C, 58.91; H, 6.72.

4-Ethyl-7-methylthieno[2,3-c]pyridin-5-ol

Acetic anhydride (2.8 ml, 29.4 mmol) was added to a solution of perchloric acid (70%, 230 mg, 1.61 mmol) in methyl 2-(thien-3-yl)butanoate (4.33 g, 23.5 mmol) at 0° C. The reaction was stirred at room temperature for 0.5 hour, diluted with CH$_2$Cl$_2$ (50 ml), and washed with saturated aqueous NaHCO$_3$. The organic phase was dried over MgSO$_4$ and evaporated in vacuo to give an oil which is a mixture of acetyl thiophenes (5.1 g, 96% yield) and was used without purification in the next step. IR (KBr) 2960, 1730 and 1660 cm$^{-1}$; mass spectrum m/z 226 (M+); $^1$H NMR (CDCl$_3$) δ0.90 (t, J=8 Hz, CH$_2$C$\underline{H}$$_3$), 1.60–2.27 (m, C$\underline{H}$$_2$,CH$_3$), 2.53 (s, COCH$_3$), 3.65 and 3.68 each (s, 3H, CO$_2$C$\underline{H}$$_3$), 4.78 (t, 1H, J=7 Hz, C$\underline{H}$CH$_2$), 7.00 to 7.63 (m, thiophene-H).

The above mixture of acetyl thiophenes (5.1 g, 22.5 mmol) was added to molten ammonium acetate at 120° C. Ammonia was bubbled into the mixture and the temperature was maintained at 120° C. for 40 minutes. The hot mixture was poured into 400 ml of ice water, and a sticky semisolid precipitated. The water was decanted, the semisolid was dissolved in hot isopropanol (40 ml) and the product, which crystallized upon cooling, was collected by filtration and triturated with Et$_2$O to give the product (1.3 g, 29% yield) as a yellow solid; mp 187°–189° C.; IR (KBr) 1630 cm$^{-1}$; mass spectrum m/z 193 (M+); $^1$H NMR (TFA) δ1.37 (t, J=8 Hz, 3H, CH$_2$CH$_3$), 2.97 (s, 3H, 7-CH$_3$), 3.12 (q, J=8 Hz, 2H, CH$_2$CH$_3$), 7.63 and 8.27 each (d, J=5 Hz, 1H, thiophene-H).

Theor. C$_{10}$H$_{11}$NOS: C, 62.15; H, 5.74; N, 7.25; S, 16.59. Found: C, 62.28; H, 5.91; N, 7.17; S, 16.51.

When, in the above procedure, iodomethane, 1-iodobutane or 1-iodohexane is utilized in place of ethyl iodide, the corresponding 4-methyl, 4-butyl or 4-hexyl derivative is obtained.

EXAMPLE 3

Dimethyl 3-thiophene malonate n-Butyllithium (1.6M, 40.4 ml, 64.6 mmol) was added to a solution of diisopropylamine (9.4 ml, 6.7 mmol) in THF (90 ml) at 0°–10° C. This solution was stirred for 0.5 hour at −10° C. and cooled to −78° C. Methyl 3-thiophene acetate (10.0 g, 64 mmol) dissolved in THF (20 ml) was slowly added and stirring was continued at −78° C. for one hour. Methyl chloroformate (5.7 ml, 73.6 mmol) was slowly added (the temperature rose to −55° C.), and the mixture was stirred at −78° C. for 0.5 hour, warmed to room temperature, and stirred for two more hours. The mixture was poured into CH$_2$Cl$_2$ (400 ml) containing some ice and the separated organic phase was washed with 1N HCl and dried over MgSO$_4$. The solvent was removed in vacuo and the crude material was purified by flash chromatography on silica gel 60 (350 g) eluted with 8% EtOAc in hexanes to give the product (8.0 g, 58% yield) as an oil; IR (neat) 3115, 2960, 1740 and 1435 cm$^{-1}$; mass spectrum m/z 214 (M+); $^1$H NMR (CDCl$_3$) δ 3.73 (s, 6H, CO$_2$CH$_3$), 4.75 [s, 1H, CH(CO$_2$CH$_3$)$_2$], 7.03 to 7.30 (m, 3H, 2, 4 and 5 thiophen-H).

Theor. C$_9$H$_{10}$O$_4$S: C, 50.46; H, 4.70. Found: C, 50.25; H, 4.49.

Dimethyl 2-acetyl-3-thiophene malonate

Dimethyl 3-thiophene malonate (5.86 g, 27.4 mmol) and perchloric acid (70%, 260 mg, 1.8 mmol) were treated with acid ahydride (3.1 ml, 32.8 mmol) at 0° C. The mixture was stirred at room temperature for 45 minutes, diluted with saturated aqueous NaHCO$_3$, and extracted with CH$_2$Cl$_2$ (2×100 ml). The combined organic layers were dried over MgSO$_4$, the solvent was removed in vacuo, and the resultant oil was purified by flash chromatography on silica gel 60 (250 g) eluted with 35% EtOAc in hexanes to give the product (1.6 g, 23% yield) as an oil; $^1$H NMR (CDCl$_3$) δ 2.55 (s, 3H, COCH$_3$), 3.77 (s, 6H, CO$_2$CH$_3$), 5.98 [s, 1H, CH(CO$_2$CH$_3$)$_2$], 7.25 and 7.51 each (d, J=5 Hz, 1H, thiophene-H).

4-Carbomethoxy-7-methylthieno[2,3-c]pyridin-5-o]

Dimethyl 2-acetyl 3-thiophene malonate (1.64 g, 6.4 mmol), was dissolved in isopropanol (about 20 ml) and added to molten NH$_4$OAc at 140° C. The reaction mixture was stirred for 35 minutes at 130°–140° C. and the melt was poured into ice water (200 ml). The yellow-green precipitate was collected by filtration, washed with H$_2$O and recrystallized from isopropanol to give the product (0.702 g, 49% yield) as a yellow solid; mp 187°–190° C.; IR (KBr) 1710 and 1595 cm$^{-1}$; mass spectrum m/z 223 (M+); $^1$H NMR (CDCl$_3$) δ 2.73 (s, 3H, 7-CH$_3$), 4.05 (s, 3H, CO$_2$CH$_3$), 7.70 and 7.83 each (d, J=5 Hz, 1H, 2- and 3-thiophene-H), 12.08 (brs, 1H, exchanges with D$_2$O, O-H).

Theor. C$_{10}$H$_9$NO$_3$S: C, 53.80; H, 4.06; N, 6.27. Found: C, 53.75; H, 4.07; N, 6.28.

The 4-carboethoxy or 4-carbopropoxy derivative is prepared analogously using the appropriate chloroformate.

EXAMPLE 4

4-Bromo-7-methylthieno[2,3-c]pyridin-5-ol

Bromine (0.65 ml, 12.7 mmol) was added to a solution of 7-methylthieno[2,3-c]pyridin-5-ol (2.00 g, 12.1 mmol) and sodium acetate (1.5 g, 18.7 mmol) in acetic acid (30 ml) at room temperature. A yellow solid precipitated. The reaction was stirred for one hour at room temperature, and the precipitate collected by filtration and washed with acetic acid. The solid was triturated successively in H$_2$O, acetone, and Et$_2$O, collected by filtration and dried in vacuo to give the product (1.72 g, 58% yield) as a yellow solid; mp 196°–198° C. (dec); IR (KBr) 1640 cm$^{-1}$; mass spectrum m/z 243 (M+); $^1$H NMR (TFH) δ 3.00 (s, 3H, CH$_3$), 7.71 and 8.45 each (d, J=5 Hz, 1H, thiophene-H).

For C$_8$H$_6$BrNOS: Theor. C, 39.36; H, 2.48; N, 5.74; S, 13.14; Br, 32.73. Found: C, 39.17; H, 2.49; N, 5.62; S, 13.21; Br, 32.64.

EXAMPLE 5

4-Chloro-7-methylthieno[2,3-c]pyridin-5-ol

Sulfuryl chloride (1.75 ml, 18.7 mmol) was added over one minute to a solution of 7-methylthieno[2,3-c]pyridin-5-ol (3.00 g, 18.2 mmol) in glacial acetic acid (30 ml) at 15° C. The reaction was stirred at room temperature for three hours, and a pale green precipitate formed. The solid was collected by filtration and washed with acetic acid. The filtrates were evaporated in vacuo, and the solid residue was combined with the precipitate and purified using flash chromatography on silica gel 60 (120 g) eluted with 2% MeOH in CH$_2$Cl$_2$ to give the product (0.64 g, 18% yield) as a yellow solid; mp 272°–275° C.; IR (KBr) 1645, 1620, 1490 and 1460 cm$^{-1}$; mass spectrum m/z 199 (M+); $^1$H NMR (DMSO-d$_6$) δ 2.52 (s, 3H, 7-CH$_3$), 7.20 (d, J=5 Hz, 1H, thiophene-H), 8.07 (d, J=5 Hz, 1H, thiophene-H), 12.10 (b.s., 1H, —OH).

Theor. C$_8$H$_6$ClNOS: C, 48.13; H, 3.03; N, 7.02. Found: C, 48.13; H, 3.00; N, 7.02.

EXAMPLE 6

7-Methyl-4-nitrothieno[2,3-c]pyridin-5-ol

Nitric acid (90%, 3.2 ml, 75 mmol) was added over a period of three minutes to a solution of 7-methylthieno[2,3-c]pyridin-5-ol (2.0 g, 12.1 mmol) in acetic acid (25 ml) at 15° C. A yellow solid precipitated. The mixture was stirred at room temperature for 20 minutes. The precipitate was collected by filtration, washed sparingly with acetic acid, triturated in Et$_2$O, filtered and dried in vacuo to give the product (1.70 g, 67% yield) as a bright yellow solid; mp 275°–278° C. (dec); IR (KBr) 1660, 1600 and 1490 cm$^{-1}$; mass spectrum m/z 210 (M+); $^1$H NMR (TFA) δ 3.28 (s, 3H, CH$_3$), 8.65 and 8.95 each (d, J=5 Hz, 1H, thiophene-H).

Theor. C$_8$H$_6$N$_2$O$_3$S: C, 45.71; H, 2.88; N, 13.33; S, 15.25. Found: C, 45.64; H, 2.89; N, 13.26; S, 15.19.

EXAMPLE 7

4-Amino-7-methylthieno[2,3-c]pyridin-5-ol

7-Methyl-4-nitrothieno[2,3-c]pyridin-5-ol (2.5 g, 11.9 mmol) was suspended in methanol (150 ml) containing Pd/C (10%, 250 mg) and was hydrogenated at 40 psi for 30 minutes in a Parr apparatus. The mixture was filtered through celite, and the collected solid was washed with methanol (100 ml). The filtrates were concentrated to 50 ml in vacuo, and a solid crystallized from solution. The yellow crystals were collected by filtration, washed with cold methanol and air-dried to give the product (1.4 g, 65% yield); mp 203°–205° C. (dec); IR (KBr) 1635 and 1440 cm$^{-1}$; mass spectrum m/z 180 (M+); $^1$H NMR (Me$_2$SO-d$_6$) δ 2.33 (s, 3H, 7-C$\underline{H}_3$), 5.23 (b.s. exchanges in D$_2$O, 2H, N$\underline{H}_2$), 7.28 and 7.48 each (d, J=6 Hz, 1H, thiophene-$\underline{H}$), 11.8 (b.s., exchanges in D$_2$O, 1H, O$\underline{H}$).

Theor. C$_8$H$_8$N$_2$O.¼H$_2$O: C, 52.02; H, 4.64; N, 15.16. Found: C, 52.18; H, 4.49; N, 15.05.

EXAMPLE 8

4-Acetamido-7-methylthieno[2,3-c]pyridin-5-ol

Acetic anhydride (1.1 ml, 11.7 mmol) was added to a solution of 4-amino-7-methylthieno[2,3-c]pyridin-5-ol (2.0 g, 11.1 mmol) in acetic acid (15 ml). The solution was stirred for 0.5 hour at room temperature and the solvent removed in vacuo at 40° C. The yellow solid residue was triturated successively with acetone, ether, refluxing methanol and ether to give the product (1.8 g, 72% yield) as a yellow solid; mp>290° C.; IR (KBr) 3280, 1635 and 1530 cm$^{-1}$; mass spectrum m/z 222 (M+); UV (EtOH) λ: 226 nm (ε=21960); $^1$H NMR (TFA) δ 2.58 (s, 3H, COC$\underline{H}_3$), 3.02 (s, 3H, 7-C$\underline{H}_3$), 7.68 and 8.37 each (d, J=5 Hz, 1H, thiophene-$\underline{H}$).

Theor. C$_{10}$H$_{10}$N$_2$O$_2$S.¼H$_2$O: C, 52.96; $\overline{H}$, 4.67; H, 12.35. Found: C, 53.38; H, 4.39; N, 12.30.

Alternatively, the 4-acetamido derivative is prepared by treating the 4-amino derivative with acetyl chloride in methylene chloride and in the presence of triethylamine. Analogously, the corresponding 4-benzamido derivatives are prepared by using benzoyl chloride, 4-chlorobenzoyl chloride, p-anisoyl chloride and p-toluoyl chloride. When ethyl chloroformate is employed in place of acetyl chloride, the 4-carboxyethylcarbamoyl-5-hydroxy-7-methylthieno[2,3-c]pyridine derivative is obtained.

EXAMPLE 9

5-Hydroxy-7-methyl-4-ureidothieno[2,3-c]pyridine

Sodium cyanate (0.865 g, 13 mmol) was added to a solution of 4-amino-7-methylthieno[2,3-c]pyridin-5-ol (2.00 g, 11.1 mmol) in acetic acid (25 ml). A yellow solid precipitated within five minutes. The mixture was stirred for 20 minutes and filtered. The solid product was triturated successively with H$_2$O, acetone, and Et$_2$O, and dried in vacuo to give the product (1.81 g, 73% yield) as a yellow solid; mp 261°–265° C. (dec); IR (KBr) 3425, 3255, 1630 and 1540 cm$^{-1}$; mass spectrum m/z 224 (MH+); $^1$H NMR (TFA) δ 3.02 (s, 3H, 7-C$\underline{H}_3$), 8.25 (b.s., 1H, N$\underline{H}$), 7.68 and 8.38 each (d, J=5 Hz, 1H, thiophene-$\underline{H}$).

Theor. $\overline{C}_9$H$_9$N$_3$O$_2$S: C, 48.42; H, 4.06; N, 18.82; S, 14.36. Found: C, 48.19; H, 3.86; N, 18.76; S, 14.40.

EXAMPLE 10

5-Hydroxy-4-(2-methoxyphenylureylene)-7-methyl-thieno[2,3-c]pyridine

2-Methoxyphenylisocyanate (0.9 ml, 6.77 mmol) was added to a solution of 4-amino-7-methylthieno[2,3-c]pyridin-5-ol (1.1 g, 6.10 mmol) in acetic acid (20 ml). A solid precipitated immediately and the mixture was stirred for one hour at room temperature. The solid was collected by filtration, washed with acetic acid and triturated successively with Et$_2$O refluxing EtOH, and refluxing Et$_2$O to give the product (0.780 g, 39% yield) as a yellow solid; mp 139°–144° C. (dec); IR (KBr) 1550, 1605, 1635, 2300–3600 and 3300 cm$^{-1}$; mass spectrum m/z 329 (M+); $^1$H NMR (TFA) δ 3.00 (s, 3H, 7-C$\underline{H}_3$), 4.00 (s, 3H, OC$\underline{H}_3$), 6.93–7.83 (m, 5H, Ar-$\underline{H}$ and thiophene-$\underline{H}$), 8.37 (d, J=5 Hz, 1H, thiophene-$\underline{H}$).

Theor. C$_{16}$H$_{15}$N$_3$O$_3$S: C, 58.34; H, 4.59; N, 12.76; S, 9.73. Found: C, 58.00; H, 4.61; N, 12.64; S, 9.81.

When, in the above procedure, methyl isocyanate, butyl isocyanate or 4-methylphenyl isocyanate is utilized, the corresponding methylureylene, butylureylene or 4-methylphenylureylene derivative is obtained.

EXAMPLE 11

4-[(3-Chlorophenyl)ureylene]-5-hydroxy-7-methyl-thieno[2,3-c]pyridine

7-Methyl-4-nitrothieno[2,3-c]pyridin-5-ol (2.48 g, 11.8 mmol) suspended in acetic acid (60 ml) was hydrogenated using 10% Pd/C (280 mg) as catalyst at 40 psi of H$_2$ for one hour on a Parr shaker. The catalyst was removed by filtration and m-chlorophenylisocyanate (1.6 ml, 12.8 mmol) was added to the filtrate. Within 15 minutes a yellow solid had precipitated. The reaction mixture was stirred at room temperature for two hours and the yellow precipitate was collected by filtration, washed with acetic acid, triturated in acetone, washed with Et$_2$O and dried in vacuo to give the product (2.8 g, 70% yield) as a yellow solid; mp 259°–262° C. (dec); IR (KBr) 1550, 1630 and 3280 cm$^{-1}$; mass spectrum m/z 334 (MH+); $^1$H NMR (TFA) δ 2.98 (s, 3H, —C$\underline{H}_3$), 7.30 (m, 3H, Ar-$\underline{H}$), 7.47 (s, 1H, Ar-$\underline{H}$), 7.63 and 8.30 each (d, J=5 Hz, 1H, thiophene-$\underline{H}$).

For C$_{15}$H$_{12}$ClN$_3$O$_2$S.¼H$_2$O: Theor. C, 53.26; H, 3.72; N, 12.42; Cl, 10.48; S, 9.48. Found: C, 53.27; H, 3.72; N, 12.45; Cl, 10.33; S, 9.67.

EXAMPLE 12

4-[(4-Chlorophenyl)ureylene]-5-hydroxy-7-methyl-thieno[2,3-c]pyridine p-Chlorophenylisocyanate (0.83 ml, 6.51 mmol) was added to a solution of 4-amino-7-methylthieno[2,3-c]pyridin-5-ol (1.1 g, 6.10 mmol) in acetic acid (20 ml) and a solid precipitated immediately. The mixture was stirred at room temperature for one hour, and the yellow solid was collected by filtration, washed with acetic acid, Et$_2$O, and triturated with refluxing EtOH and refluxing Et$_2$O and dried in vacuo to give the product (1.2 g, 55% yield) as a yellow solid; mp 164°–166° C. (dec); IR (KBr) 1545, 1640 and 3300 cm$^{-1}$; mass spectrum m/z 206 (M-C$_6$H$_6$NCl+); $^1$H NMR (TFA) δ 2.97 (s, 3H, 7-C$\underline{H}_3$), 7.37 (s, 4H, Ar-$\underline{H}$), 7.63 (d, J=5 Hz, 1H, thiophene-$\overline{\underline{H}}$), 8.33 (d, J=5 Hz, 1H, thiophene-$\underline{H}$).

For C$_{15}$H$_{12}$ClN$_3$O$_2$S: Theor. C, 53.97; H, 3.62; N, 12.50; S, 9.60; Cl, 10.62. Found: C, 53.73; H, 3.75; N, 12.45; S, 9.66; Cl, 10.60.

EXAMPLE 13

5-Hydroxy-4-[(3-methoxyphenyl)ureylene]-7-methylthieno[2,3-c]pyridine m-Methoxyphenylisocyanate (1.4 ml, 10.6 mmol) was added to a solution of 4-amino-7-methylthieno[2,3-c]pyridin-5-ol (1.7 g, 9.20 mmol) in acetic acid (25 ml) and the mixture was stirred at room temperature for four hours. The yellow precipitate was collected by filtration, washed with acetic acid, triturated in acetone, washed with $Et_2O$, and air-dried to give the product as a pale yellow solid (2.0 g, 66% yield); mp 255°–260° C. (dec); IR (KBr) 1560, 1635 and 3295 $cm^{-1}$; mass spectrum m/z 329 ($M^+$); $^1H$ NMR (TFA) δ 3.00 (s, 3H, —$CH_3$), 4.02 (s, 3H, $OCH_3$), 6.87 to 7.53 (m, 4H, Ar-$\underline{H}$), 7.63 and 8.37 each (d, J=5 Hz, 1H, thiophene-$\underline{H}$).

Theor. $C_{16}H_{15}N_3O_3S$: C, 58.34; H, 4.59; N, 12.76; S, 9.73. Found: C, 57.93; H, 4.63; N, 12.51; S, 9.62.

EXAMPLE 14

5-Hydroxy-4-[(4-methoxyphenyl)ureylene]-7-methylthieno[2,3-c]pyridine p-Methoxyphenylisocyanate (1.4 ml, 10.5 mmol) was added to a solution of 4-amino-7-methylthieno[2,3-c]pyridin-5-ol (1.75 g, 9.71 mmol) in acetic acid (25 ml). Within five minutes, a yellow solid precipitated. The mixture was stirred at room temperature for three hours. The yellow precipitate was collected by filtration, washed with acetic acid, triturated in acetone, washed with $Et_2O$, and air-dried to give the product (2.15 g, 67% yield) as a pale yellow solid; mp 284°–286° C. (dec); IR (KBr) 1540, 1630, 3280 $cm^{-1}$; mass spectrum m/z 329 ($M^+$); $^1H$ NMR (TFA) δ 3.02 (s, 3H, 7-$CH_3$), 4.03 (s, 3H, $OCH_3$), 7.15 (d, J=7 Hz, 2H, Ar-$\underline{H}$), 7.45 (d, J=7 Hz, 2$\underline{H}$, Ar-$\underline{H}$), 7.60 and 8.38 each (d, $\overline{J}$=5 Hz, 1H, thiophene-$\underline{H}$).

Theor. $C_{16}H_{15}N_3O_3S$: C, 58.34; H, 4.59; N, 12.76; S, 9.73. Found: C, 58.14; H, 4.54; N, 12.49; S, 9.70.

EXAMPLE 15

5-Hydroxy-4-[(2,4-dimethoxyphenyl)ureylene]-7-methylthieno[2,3-c]pyridine

A suspension of 7-methyl-4-nitrothieno[2,3-c]pyridin-5-ol (6.0 g, 28.5 mmol) in acetic acid (100 ml) was hydrogenated using 10% Pd/C (500 mg) as catalyst at 40 psi of $H_2$ for one hour at room temperature in a Parr shaker. The catalyst was removed by filtration through a pad of celite and the celite was washed with 50 ml of acetic acid. The combined organics filtrated (150 ml) were divided and aliquots were used in subsequent reactions. 2,4-Dimethoxyphenylisocyanate (1.9 g, 10.6 mmol) in acetic acid (20 ml) was added to a solution of the above aminopyridinol in acetic acid (50 ml, 9.5 mmol), and the mixture was stirred at room temperature for 18 hours. The pale yellow precipitate was collected by filtration, washed with acetic acid, triturated in acetone, washed with $Et_2O$ and air-dried to give the product (1.58 g, 46% yield) as a pale yellow solid; mp 237°–240° C. (dec); IR (KBr) 1550, 1635 and 3280 $cm^{-1}$; mass spectrum m/z 360 ($MH^+$); $^1H$ NMR (TFA) δ 3.00 (s, 3H, $CH_3$), 3.98 (s, 3H, $OCH_3$), 4.02 (s, 3H, $OCH_3$), 6.78 (s, 1$\underline{H}$, Ar-$\underline{H}$), 7.43 (s, 1$\underline{H}$, Ar-$\underline{H}$), 7.60 and 8.33 each (d, J=5 Hz, 1H, thiophene-$\underline{H}$).

Theor. $C_{17}H_{17}N_3O_4S$: C, 56.81; H, 4.77; N, 11.69; S, 8.92. Found: C, 56.75; H, 4.89; N, 11.41; S, 8.77.

EXAMPLE 16

5-Hydroxy-4-[(3,5-dimethoxyphenyl)ureylene]-7-methylthieno[2,3-c]pyridine 3,5-Dimethoxyphenylisocyanate (2.0 g, 11.2 mmol) in acetic acid (20 ml) was added to a solution of the above aminopyridinol (Example 15) in acetic acid (50 ml, 9.5 mmol). The mixture was stirred at room temperature for 18 hours. The bright yellow precipitate was collected by filtration, washed with acetic acid, triturated with acetone, washed with $Et_2O$ and air-dried to give the product (2.9 g, 85% yield) as a bright yellow solid; mp 243°–246° C. (dec); IR (KBr) 1560, 1640 and 3300 $cm^{-1}$; mass spectrum m/z 360 ($MH^+$); $^1H$ NMR (TFA) δ 3.00 (s, 3H, $CH_3$), 4.00 (s, 6H, $OCH_3$), 6.67 (b.s., 1H, Ar-$\underline{H}$), 6.83 (b.s., 2H, Ar-$\underline{H}$), 7.67 and 8.37 each (d, J=5 Hz, 1H, thiophene-$\underline{H}$).

Theor. $C_{17}H_{17}N_3O_4S$: C, 56.81; H, 4.77; N, 11.69; S, 8.92. Found: C, 56.89; H, 4.95; N, 11.58; S, 9.02.

EXAMPLE 17

5-Hydroxy-4-[(2,5-dimethoxyphenyl)ureylene]-7-methylthieno[2,3-c]pyridine 2,5-Dimethoxyphenylisocyanate (1.9 g, 10.6 mmol) in acetic acid (20 ml) was added to the above solution of aminopyridinol (Example 15) in acetic acid (50 ml, 9.5 mmol), and the reaction mixture was stirred for 18 hours at room temperature. The bright yellow precipitate was collected by filtration, washed with acetic acid, triturated with acetone, washed with $Et_2O$ and air-dried to give the product (1.8 g, 53% yield) as a bright yellow solid; mp 218°–222° C. (dec); IR (KBr) 1540, 1645 and 3280 and 3360 $cm^{-1}$; mass spectrum m/z 360 ($MH^+$); $^1H$ NMR (TFA) δ 3.00 (s, 3H, 7-$CH_3$), 3.97 (s, 3H, $OCH_3$), 4.00 (s, 3H, $OCH_3$), 7.00 (s, 2$\underline{H}$, Ar-$\underline{H}$), 7.57 (s, 1H, Ar-$\underline{H}$), 7.68 and 8.35 each (d, J=6 Hz, 1H, thiophene-$\underline{H}$).

Theor. $C_{17}H_{17}N_3O_4S$: C, 56.81; H, 4.77; N, 11.69; S, 8.92. Found: C, 56.60; H, 4.75; N, 11.48; S, 9.05.

EXAMPLE 18

4-Ethyl-7-methyl-5-[3-(N,N-dimethylamino)propoxy]-thieno[2,3-c]pyridine 3-(N,N-Dimethylamino)propylchloride hydrochloride (5.51 g, 34.9 mmol) and sodium hydride (60% in oil, 1.55 g, 38.8 mmol, prewashed with pentane) in DMF (30 ml) were stirred at room temperature for one hour. This solution was then added to a mixture of 4-ethyl-7-methylthieno[2,3-c]pyridin-5-ol (2.9 g, 15.0 mmol) and sodium hydride (60% in oil, 0.60 g, 15.0 mmol, prewashed in pentane) in DMF (30 ml) which had been allowed to react for two hours. The combination was stirred at room temperature for three days, poured into $H_2O$ (500 ml), extracted with $CH_2Cl_2$ (3×200 ml) and dried over $MgSO_4$. The solvent was removed in vacuo and the product was purified by flash chromatography on silica gel 60 (120 g) using 8% MeOH in $CH_2Cl_2$ as the eluant to give the product (2.3 g, 55% yield) as a yellow oil; IR (neat) 1440, 1580 and 2980 $cm^{-1}$; mass spectrum m/z 279 ($MH^+$); $^1H$ NMR ($CDCl_3$) δ 1.20 (t, J=7 Hz, 3H, $CH_2CH_3$), 1.68 to 2.90 (m, 6H, $CH_2CH_2N$, $CH_2CH_3$), 2.27 (s, 6$\underline{H}$, $N(CH_3)_2$), 2.63 (s, 3$\overline{H}$, 7-$\overline{CH}_3$), 4.43 (t, J=6 Hz, 1H, $OCH_2\overline{CH}_2$), 7.27 and 7.53 each (d, J=6 Hz, 1H, thiophene-$\overline{H}$).

Theor. $C_{15}H_{22}N_2OS$: $\overline{C}$, 64.71; H, 7.96; N, 10.06; S, 11.52. Found: C, 64.78; H, 8.15; N, 10.02; S, 11.82.

EXAMPLE 19

4-Ethyl-7-methyl-5-[2-(N,N-dimethylamino)ethoxy]-thieno[2,3-c]pyridine

4-Ethyl-7-methylthieno[2,3-c]pyridin-5-ol (2.00 g, 10.3 mmol) was added to a suspension of NaH (60% in oil, prewashed with hexanes, 0.46 g, 11.4 mmol) in DMF (30 ml) and stirred at room temperature for two hours. To this was added a mixture of dimethylaminoethylchloride hydrochloride (3.0 g, 20.6 mmol) and NaH (60% in oil, prewashed with hexanes, 546 mg, 22.8 mmol) in DMF (30 ml). The reaction mixture was stirred for two days at room temperature, poured into $H_2O$ (300 ml) and extracted with $CH_2Cl_2$ (3×200 ml). The combined organic phases were washed with $H_2O$ (2×200 ml) and dried over $MgSO_4$. The solvent was removed in vacuo to give an oil (3 g), which was purified by flash chromatography on silica gel 60 (100 g) eluted with 7% MeOH in $CH_2Cl_2$ to give an oil (1.5 g, 56% yield). The product was dissolved in $CH_2Cl_2$ (100 ml), washed with 1N aqueous NaOH (2×100 ml) and dried over $MgSO_4$. The solvent was removed in vacuo to give the product (0.950 g, 35% yield) as a yellow oil; IR (neat) 1590 and 1440 cm$^{-1}$; mass spectrum m/z 264 (M+); $^1$H NMR (CDCl$_3$) δ 1.18 (t, J=7 Hz, 3H, CH$_2$CH$_3$), 2.35 (s, 6H, N(CH$_3$)$_2$), 2.63 (s, 3H, 7-CH$_3$), 2.63-3.10 (m, 4H, CH$_2$CH$_2$N, CH$_2$CH$_3$), 4.53 (t, J=6 Hz, 2H, CH$_2$CH$_2$N), 7.27 and 7.53 each (d, J=5 Hz, 1H, thiophene-H).

Theor. $C_{14}H_{20}N_2OS$: C, 63.60; H, 7.62; N, 10.60; S, 12.13. Found: C, 63.31; H, 7.27; N, 10.43; S, 12.19.

The corresponding 5-N,N-dimethylaminoalkoxy derivatives of the compounds prepared in any of the preceding Examples 1–17 or subsequent Examples 20–24 and 39, and the corresponding 6-N,N-dimethylaminoalkyl derivatives of the compounds prepared in any of the subsequent Examples 28–37 are prepared in an analogous manner using the materials of these examples as starting materials.

EXAMPLE 20

7-Bromomethyl-4-ethyl-5-hydroxythieno[2,3-c]pyridine

Bromine (0.42 ml, 8.19 mmol) was added dropwise to a solution of 4-ethyl-7-methylthieno[2,3-c]pyridin-5-ol (1.5 g, 7.76 mmol) and sodium acetate (1.58 g, 11.6 mmol) in acetic acid (40 ml). The solution was stirred at room temperature for 0.5 hour. The solvent was removed in vacuo and the residue was triturated with $H_2O$ and air-dried. After trituration with Et$_2$O and refluxing EtOH, the solid was dried in vacuo to give the product (1.1 g, 52% yield) as yellow needles; mp 164°–166° C.; IR (KBr) 2975, 1645, 1630, 1580 and 1410 cm$^{-1}$; mass spectrum m/z 271 (M+); $^1$H NMR (Me$_2$SO-d$_6$) δ 1.13 (t, J=7 Hz, 3H, CH$_2$CH$_3$), 2.82 (q, J=7 Hz, 2H, CH$_2$CH$_3$), 4.75 (s, 2H, CH$_2$Br), 7.47 and 7.98 each (d, J=5 Hz, 1H, thiophene-H), 9.57 (b.s., 1H, OH).

For $C_{10}H_{10}BrNOS$: Theor. C, 44.13; H, 3.70; N, 5.14; S, 11.98; Br, 29.35. Found: C, 43.89; H, 3.67; N, 5.23; S, 11.77; Br, 29.01.

The corresponding 7-bromomethyl derivatives of the compounds prepared in Examples 1–19, 25–27, 39 and 40, and the corresponding 4-bromomethyl derivatives of the compounds prepared in Examples 28–38 are prepared in an analogous manner using the materials of these examples as starting materials.

EXAMPLE 21

4-Ethyl-7-[[4-(2-methoxyphenyl)piperazin-1-yl]methyl]thieno[2,3-c]pyridin-5-ol 1-(2-Methoxyphenyl)piperazine (1.6 g, 8.26 mmol) was added to a solution of 7-bromomethyl-4-ethyl-5-hydroxythieno[2,3-c]pyridine (750 mg, 2.76 mmol) in DMF (30 ml). The mixture was stirred at room temperature for 1.5 hours and the solvent was removed in vacuo. The residue was triturated with $H_2O$ to give a pale yellow solid which was collected by filtration, washed with $H_2O$, triturated with refluxing EtOH and with Et$_2$O to give the product (1.0 g, 94% yield) as a pale yellow solid; mp 230°–233° C. (dec); IR (KBr) 1580, 1635, 2200–3180 and 2840 cm$^{-1}$; mass spectrum m/z 383 (M+); $^1$H NMR (TFA) δ 1.38 (t, J=7 Hz, 3H, CH$_2$CH$_3$), 3.18 (q, J=7 Hz, 2H, CH$_2$CH$_3$), 4.01 (s, 3H, OCH$_3$), 4.32 (s, 8H, N—CH$_2$—CH$_2$N), 5.12 (s, 2H, 7—CH$_2$—N), 6.98-7.75 1 (m, 4H, Ar-H), 7.65 (d, J=5 Hz, 1H, thiophene-H), 8.28 (d, J=5 Hz, 1H, thiophene-H).

Theor. $C_{21}H_{25}N_3O_2S$: C, 65.77; H, 6.57; N, 10.96; S, 8.36. Found: C, 65.68; H, 6.62; N, 10.91; S, 8.38.

The corresponding [4-(2-methoxyphenyl)piperazin-1-yl]methyl derivatives of the compounds prepared in Examples 1–19, 25–27, 39 and 40, and the corresponding [4-(2-methoxyphenyl)piperazin-1-yl]methyl derivatives of the compounds prepared in Examples 28–38 are prepared in an analogous manner using the materials of these examples as starting materials.

EXAMPLE 22

4-Ethyl-7-[[4-(2-methylphenyl)piperazin-1-yl]methyl]-thieno[2,3-c]pyridin-5-ol A mixture of 7-bromomethyl-4-ethyl-5-hydroxythieno[2,3-c]pyridine (1.2 g, 4.4 mmol), 1-(2-tolyl)piperazine hydrochloride (1.9 g, 8.8 mmol) and NaHCO$_3$ (1.09 g, 13.2 mmol) in DMF was stirred at room temperature for three days. The mixture was poured into ice water (200 ml) and the pale yellow precipitate was collected by filtration, washed with $H_2O$, triturated with hot EtOH, and then Et$_2$O and dried in vacuo to give the product (0.69 g, 43% yield) as a pale yellow solid; mp 217°–220° C.; IR (KBr) 1635 and 1575 cm$^{-1}$; mass spectrum m/z 368 (M+); $^1$H NMR (TFA) δ1.40 (t, J=8 Hz, 3H, CH$_2$CH$_3$), 2.60 (s, 3H, Ar-CH$_3$), 3.18 (q, J=8 Hz, 2H, CH$_2$CH$_3$), 4.13-4.50 (m, 8H, NCH$_2$CH$_2$N), 5.10 (s, 2H, 7-CH$_2$N), 7.53 (s, 4H, Ar-H), 7.70 and 8.33 each (d, J=5 Hz, 1H, thiophene-H).

For $C_{21}H_{25}N_3OS \cdot \frac{1}{2}H_2O$: Theor. C, 66.99; H, 6.96; N, 11.15; S, 8.52. Found: C, 66.84; H, 6.97; N, 11.14; S, 8.48.

The corresponding [4-(2-methylphenyl)piperazin-1-yl]methyl derivatives of the compounds prepared in Examples 1–19, 25–27, 39 and 40, and the corresponding [4-(2-methylphenyl)piperazin-1-yl]methyl derivatives of the compounds prepared in Examples 28–38 are prepared in an analogous manner using the materials of these examples as starting materials.

EXAMPLE 23

7-Bromomethyl-4-bromothieno[2,3-c]pyridin-5-ol

Bromine (1.3 ml, 25.4 mmol) was added dropwise to a solution of 7-methylthieno[2,3-c]pyridin-5-ol (2.0 g, 12.1 mmol) and sodium acetate (6.6 g, 48.5 mmol) in acetic acid (45 ml). Within minutes a yellow solid had precipitated. The reaction mixture was stirred at room temperature for two hours, and the solid was collected by filtration, washed with acetic acid, Et$_2$O and air-dried to give the product (1.78 g, 46% yield); mp 185°–186° C. (dec); IR (KBr) 1625, 1590 and 1540 cm$^{-1}$; mass spectrum m/z 321 (M+); $^1$H NMR (Me$_2$SO-d$_6$) δ4.78 (s, 2H, CH$_2$Br), 7.33 and 8.17 each (d, J=5 Hz, 1H, thiophene-H).

EXAMPLE 24

4-Bromo-7-[[4-(2-methoxyphenyl)piperazin-1-yl]methyl]thieno[2,3-c]pyridin-5-ol 1-(2-Methoxyphenyl)piperazine (2.7 g, 13.9 mmol) was added to a solution of 7-bromomethyl-4-bromo-thieno[2,3-c]pyridin-5-ol (1.5 g, 4.6 mmol) in DMF (25 ml) and stirred at room temperature for one hour. The reaction mixture was poured into H$_2$O (100 ml). The yellow solid precipitate was collected by filtration, washed generously with H$_2$O, triturated with acetone, Et$_2$O and air-dried to give the product (1.9 g, 94% yield) as a yellow solid; mp 229°–231° C. (dec); IR (KBr) 1635 and 1550 cm$^{-1}$; mass spectrum m/z 434 (MH+); $^1$H NMR (TFA) δ4.02–4.48 (m, 8H, CH$_2$N), 4.07 (s, 3H, OCH$_3$), 5.02 (s, 2H, Ar-CH$_2$N), 7.15–7.83 (m, 5H, Ar-H, thiophene-H), 8.33 (d, J=5 Hz, 1H, thiophene-H).

For C$_{19}$H$_{20}$BrN$_3$O$_2$S: Theor. C, 52.54; H, 4.64; N, 9.67; Br, 18.40; S, 7.38. Found: C, 52.39; H, 4.93; N, 9.78; Br, 18.33; S, 7.45.

EXAMPLE 25

5-Acetoxy-7-methylthieno[2,3-c]pyridine

A solution of 7-methylthieno[2,3-c]pyridin-5-ol (5.0 g, 30.3 mmol) and concentrated sulfuric acid (3 drops) in acetic anhydride (50 ml) was stirred at room temperature for 16 hours. The mixture was poured into ice water (300 ml), neutralized with NaHCO$_3$, and was extracted with CH$_2$Cl$_2$. The organic layer was washed with a saturated solution of NaHCO$_3$, dried over MgSO$_4$, treated with activated charcoal and evaporated in vacuo to give the product (3.9 g, 62% yield) as an amber oil; IR (neat) 3090, 1770 and 1585 cm$^{-1}$; mass spectrum m/z 207 (M+); $^1$H NMR (CDCl$_3$) δ2.35 (s, 3H, COCH$_3$), 2.75 (s, 3H, CH$_3$), 7.28 (d superimposed on s, J=5 Hz, 2H, thiophene-H, Ar-H), 7.67 (d, J=5 Hz, 1H, thiophene-H).

Theor. C$_{10}$H$_9$NO$_2$S: C, 57.95; H, 4.38; N, 6.76. Found: C, 57.70; H, 4.33; N, 6.72.

EXAMPLE 26

5-Acetoxy-4-bromo-7-methylthieno[2,3-c]pyridine

A solution of 4-bromo-7-methylthieno[2,3-c]pyridin-5-ol (3.0 g, 12.3 mmol) and concentrated sulfuric acid (2 drops) in acetic anhydride (25 ml) was stirred at room temperature for three days. The mixture was poured into ice water (200 ml). A colorless solid precipitated which was collected by filtration, washed with H$_2$O, and air-dried. This solid was dissolved in CH$_2$Cl$_2$, treated with charcoal, and precipitated by adding hexanes to give the product (2.14 g, 61% yield) as a colorless solid; mp 132°–133° C.; IR (KBr) 3120 and 1770 cm$^{-1}$; mass spectrum m/z 243 (m-COCH$_2$+); $^1$H NMR (CDCl$_3$) δ2.42 (s, 3H, COCH$_3$), 2.73 (s, 3H, CH$_3$), 7.47 (d, J=5 Hz, 1H, thiophene-H), 7.78 (d, J=5 Hz, 1H, thiophene-H).

For C$_{10}$H$_8$BrNO$_2$S: Theor. C, 41.98; H, 2.82; N, 4.89; Br, 27.92; S, 11.21. Found: C, 41.78; H, 2.86; N, 4.82; Br, 27.99; S, 11.13.

The corresponding 5-acetoxy derivatives of the compounds prepared in any of the preceding Examples 1–17 or subsequent Examples 20–24 and 39, and the corresponding 6-acetoxy derivatives of the compounds prepared in any of the subsequent Examples 28–37 are prepared in an analogous manner using the materials of these examples as starting materials. Alternatively, the 5-acetoxy derivative or 6-acetoxy derivative for Examples 28–37 is prepared by treating the 5- or 6-hydroxy derivative with acetyl chloride in the presence of triethylamine. Analogously, the corresponding 5-benzyloxy derivatives are prepared by using benzoyl chloride, 4-chlorobenzoyl chloride, p-anisoyl chloride and p-toluoyl chloride.

EXAMPLE 27

5-Acetoxy-4-ethyl-7-methylthieno[2,3-c]pyridine

A solution of 4-ethyl-7-methylthieno[2,3-c]pyridin-5-ol (0.50 g, 2.59 mol) and concentrated sulfuric acid (1 microdrop) in acetic anhydride (5 ml) was stirred at room temperature for 16 hours. The mixture was treated with H$_2$O (20 ml), neutralized with solid NaHCO$_3$, and extracted with CH$_2$Cl$_2$ (2×50 ml). The organic layer was dried over MgSO$_4$ and eluted through a column of magnesium silicate. The eluent was concentrated to 10 ml, diluted with hexanes (20 ml), and the resultant solid was collected by filtration and washed with hexanes to give the product (0.36 g, 59% yield) as a colorless solid; mp 69°–71° C.; IR (KBr) 3070 and 1770 cm$^{-1}$; mass spectrum m/z 235 (M+); $^1$H NMR (CDCl$_3$) δ1.23 (t, J=7 Hz, 3H, CH$_2$CH$_3$), 2.38 (s, 3H, COCH$_3$), 2.27 (s, 3H, CH$_3$), 2.82 (q, J=7 Hz, 2H, CH$_2$CH$_3$), 7.40 (d, J=5 Hz, 1H, thiophene-H), 7.68 (d, J=5 Hz, 1H, thiophene-H).

Theor. C$_{12}$H$_{13}$NO$_2$S: C, 61.25; H, 5.57; N, 5.95, S, 13.63. Found: C, 61.09; H, 5.23; N, 5.98; S, 13.57.

EXAMPLE 28

1-(3-Thienyl)ethanol

3-Acetylthiophene (100 g, 0.790 mol) in Et$_2$O (600 ml) was added dropwise to a suspension of lithium aluminum hydride (15.3 g, 0.403 mol) in Et$_2$O (400 ml) over a one hour period. The mixture was heated to reflux for one hour and cooled to room temperature. H$_2$O (16 ml) was slowly added to the mixture, then 15% aqueous NaOH (16 ml) and H$_2$O (50 ml). A white solid was filtered and washed with Et$_2$O. The combined Et$_2$O filtrates were dried over MgSO$_4$ and evaporated in vacuo to give the product (101 g, 100% yield) as an oil; IR (neat) 2990 and 3040 to 3700 cm$^{-1}$; mass spectrum m/z 128 (M+); $^1$H NMR (CDCl$_3$) δ1.52 (d, J=6 Hz, 3H, CHCH$_3$), 2.08 (brs, 1H, exchanges with D$_2$O, OH), 4.95 (q, J=6 Hz, 1H, CHCH$_3$), 6.98–7.38 (m, 3H, thiophene-H).

1-(3-Thienyl)chloroethane

Thionyl chloride (95 ml, 0.819 mol) was added to 1-(3-thienyl)ethanol (100 g, 0.780 mol) at 0° C. over a one hour period. The mixture was stirred at room temperature for 2.5 hours, and ice water (300 ml) was added to the mixture. Extraction with Et$_2$O (1×600 ml, 2×200 ml) and subsequent treatment of the combined organic phases with MgSO$_4$ and charcoal, and removal of the solvent in vacuo at 40° C., gave the product (99.6 g, 87% yield) as an amber oil; IR (neat) 3100, 2980, 2940, 1440 and 1420 cm$^{-1}$; $^1$H NMR (CDCl$_3$) δ1.85 (d, J=6 Hz, 3H, CHClCH$_3$), 5.23 (q, J=6 Hz, 1H, CHClCH$_3$), 7.03-7.38 (m, 3H, thiophene-H).

4-Methylthieno[3,2-c]pyridin-6-ol 2,2-Diethoxyacetamide (106.4 g, 0.723 mol) was added in portions to a suspension of sodium hydride (60% in oil, prewashed with pentane, 29.0 g, 0.726 mol) in THF (500 ml). 1-(3-Thienyl)chloroethane (99.1 g, 0.676 mol) dissolved in THF (200 ml) was added to the above solution. Sodium iodide (10 g, 66.7 mmol) was added and the mixture was heated to reflux for 24 hours. The solvent was evaporated in vacuo. H$_2$O (300 ml) was added to the oily residue and extracted with CH$_2$Cl$_2$ (1×600 ml, 2×200 ml). The combined organic phases were dried over MgSO$_4$ and the solvent was evaporated in vacuo to give an oil (155 g) which was purified by flash chromatography on silica gel 60 (1 kg) eluted with 25% EtOAc in hexanes to give the product (70 g, 38% yield) as an oil; IR (neat) 3440, 3320, 3000, 1690 and 1520 cm$^{-1}$; mass spectrum m/z 257 (M+); $^1$H NMR (CDCl$_3$) δ1.22 and 1.23 each (t, J=7 Hz, 3H, CH$_2$CH$_3$), 1.57 (d, J=7 Hz, 3H, CHCH$_3$), 3.63 and 3.67 each (q, J=7 Hz, 2H, CH$_2$CH$_3$), 4.77 (s, 1H, COCH), 5.00-5.50 (m, 1H, NHCHCH$_3$), 6.73 (brs, 1H, NH), 6.97-7.37 (m, 3H, thiophene-H).

Theor. C$_{12}$H$_{19}$NO$_3$S: C, 56.01; H, 7.44; N, 5.44; S, 12.46. Found: C, 56.06; H, 7.76; N, 5.37; S, 12.70.

The acetal above (12.0 g, 46.6 mol) was heated to reflux in 47% HBr (40 ml) and glacial acetic acid (80 ml) for 15 minutes. The mixture was cooled to room temperature and a purple solid precipitated. The solid was collected by filtration, washed with acetic acid and Et$_2$O. It was then suspended in H$_2$O (200 ml) and neutralized with solid NaHCO$_3$, reisolated on filter, washed with H$_2$O and recrystallized from isopropanol. The product was washed with isopropanol and Et$_2$O to give an off-white solid (2.6 g, 34% yield); mp 225°-227° C.; IR (KBr) 2300-3060, 1640 and 1585 cm$^{-1}$; mass spectrum m/z 165 (M+); $^1$H NMR (TFA) δ3.05 (3, 3H, CH$_3$), 7.60 and 7.75 each (d, J=6 Hz, 1H, thiophene-H), 7.65 (s, 1H, 7-H).

Theor. C$_8$H$_7$NOS: C, 58.16; H, 4.27; N, 8.48; S, 19.41. Found: C, 58.09; H, 4.45; N, 8.24; S, 19.70.

When, in the above procedure, 3-acetyl-4-methylthiophene, 3-acetyl-5-methylthiophene, or 3-acetyl-4,5-dimethylthiophene is employed, the corresponding 3,4-dimethyl, 2,4-dimethyl or 2,3,4-trimethyl derivative is obtained.

EXAMPLE 29

Alternatively, 4-methylthieno[3,2-c]pyridin-6-ol was prepared as follows:

1-(3-Thienyl)ethylazide

A mixture of 1-(thien-3-yl)chloroethane (5.0 g, 34 mmol) and sodium azide (2.65 g, 41 mmol) in DMF was stirred at room temperature for three days. The reaction mixture was poured into H$_2$O (500 ml) and extracted with CH$_2$Cl$_2$ (3×200 ml). The organic extracts were washed with H$_2$O (5×100 ml), dried over MgSO$_4$ and concentrated in vacuo to give the product (5.02 g, 96% yield) as a brown oil; IR (neat) 2110 cm$^{-1}$; $^1$H NMR (CDCl$_3$) δ1.55 (d, J=7 Hz, 3H, CHCH$_3$), 4.67 (q, J=7 Hz, 1H, CHCH$_3$), 6.98-7.43 (m, 3H, thiophene-H).

This material was used without purification in the next step.

1-(3-Thienyl)ethylamine

A solution of the above azide (5.0 g, 32.6 mmol) in Et$_2$O (80 ml) was added to a suspension of lithium aluminum hydride (1.7 g, 44.8 mmol) in Et$_2$O (80 ml) under a nitrogen atmosphere at such a rate as to maintain a gentle reflux. An external heat source was applied to the reaction mixture and was heated to reflux for an additional hour. H$_2$O (2 ml) was added carefully to the mixture, followed by 15% NaOH in H$_2$O (2 ml) and H$_2$O (6 ml). The inorganic materials were filtered from this reaction mixture and washed with Et$_2$O. The combined organic filtrates were dried over MgSO$_4$, and the solvent was removed in vacuo to give the product (3.7 g, 90% yield) as an amber oil; IR (neat) 1590, 2760-3660 and 2990 cm$^{-1}$; mass spectrum m/z 127 (M+); $^1$H NMR (CDCl$_3$) δ1.42 (d, J=6 Hz, 3H, CHCH$_3$), 1.62 (s, 2H, exchanges with D$_2$O, NH$_2$), 4.20 (q, J=6 Hz, 1H, CHCH$_3$), 7.00-7.40 (m, 3H, thiophene-H).

This material was somewhat unstable and was used in the next step without purification.

4-Methylthieno[3,2-c]pyridin-6-ol

A standard solution of trimethylaluminum 1N in hexanes (10 ml, 20 mmol) was syringed into a solution of the above amine (2.5 g, 20 mmol) in CH$_2$Cl$_2$ (40 ml) at 0°-5° C. The solution was allowed to warm to room temperature over 0.5 hour. Ethyl 2,2-diethoxyacetate (3.6 ml, 20 mmol) was added by syringe, and the mixture was heated to reflux for two hours. 1N HCl was carefully added until the effervescence ceased. The organic layer was washed with H$_2$O, 1N HCl (1×100 ml) and dried over MgSO$_4$. The solvent was removed in vacuo to give an oil (5.05 g) of a mixture of product and ethyl 2,2-diethoxyacetate in a ratio of 3:1 as judged by TLC and $^1$H NMR analysis.

This mixture, without further purification, was treated with 48% HBr (20 ml) and glacial acetic acid (40 ml), and heated to reflux for 15 minutes. The mixture was cooled to room temperature and a precipitate was collected by filtration, washed with acetic acid and triturated with Et$_2$O to give the hydrobromide salt of the product (2.7 g, 77% yield) as a purple solid. The solid was suspended in H$_2$O (100 ml) and neutralized with solid NaHCO$_3$. An off-white solid was collected by filtration, washed with H$_2$O, and triturated with refluxing isopropanol to give the product (1.45 g, 61% yield); mp 225°-227° C.

EXAMPLE 30

7-Bromo-4-methylthieno[3,2-c]pyridin-6-ol

Bromine (0.45 ml, 8.77 mmol) was added to a solution of 4-methylthieno[3,2-c]pyridin-6-ol (1.38 g, 8.35 mmol) and sodium acetate (1.7 g, 12.5 mmol) in acetic acid. The mixture was stirred at room temperature for 30 minutes, and a solid precipitated. The solid was collected by filtration, washed with acetic acid, triturated in Et$_2$O and dried in vacuo to give the product (0.680 g, 32% yield) as an off-white solid; mp 206°-208° C. (dec); IR (KBr) 2300-3020, 1635 and 1540 cm$^{-1}$; mass spectrum m/z 243 (M+); $^1$H NMR (TFA) δ3.00 (s, 3H, CH$_3$), 7.73 (s, 2H, thiophene-H).

For C$_8$H$_6$BrNOS: Theor. C, 39.36; H, 2.48; N, 5.74; S, 13.14; Br, 32.72. Found: C, 39.54; H, 2.55; N, 5.74; S, 13.40; Br, 32.44.

EXAMPLE 31

4-Methyl-7-nitrothieno[3,2-c]pyridin-6-ol

A solution of nitric acid 90% (2.6 ml) in glacial acetic acid (5 ml) was added to a solution of 4-methyl-thieno[3,2-c]pyridin-6-ol (2.15 g, 13.0 mmol) in glacial acetic acid (30 ml) at 15°–20° C. A yellow solid precipitated immediately. The mixture was stirred for 15 minutes. The solid was collected by filtration, washed with acetic acid, triturated with refluxing EtOH and then Et$_2$O and dried in vacuo to give the product (1.66 g, 61% yield); mp 260°–273° C. (dec); IR (KBr) 2500–3040, 1675 and 1610 cm$^{-1}$; mass spectrum m/z 210 (M+); $^1$H NMR (TFA) δ3.20 (s, 3H, CH$_3$), 7.82 and 7.98 each (d, J=5 Hz, 1H, thiophene-H).

Theor. C$_8$H$_6$N$_2$O$_3$S: C, 45.71; H, 2.88; N, 13.33; S, 15.46. Found: C, 45.76; H, 2.96; N, 13.33; S, 15.25.

EXAMPLE 32

7-Amino-4-methylthieno[3,2-c]pyridin-6-ol

A suspension of 4-methyl-7-nitrothieno[3,2-c]pyridin-6-ol (6.5 g, 30.9 mmol) in acetic acid (100 ml) was hydrogenated using 10% Pd/C as catalyst in a Parr shaker at 40 psi for 20 minutes. The catalyst was removed by filtration from the reaction mixture, and the solvent was removed in vacuo to give crude product (4.7 g, 84% yield) as a tan solid; IR (KBr) 1610, 1660 and 2300–3600 cm$^{-1}$; mass spectrum m/z 180 (M+); $^1$H NMR (TFA) δ1.32 (s, 3H, CH$_3$), 7.43–7.77 (m, 2H, thiophene-H).

EXAMPLE 33

6-Hydroxy-4-methyl-7-ureidothieno[3,2-c]pyridine

Sodium cyanate (0.50 g, 7.69 mmol) was added to a solution of crude 7-amino-4-methylthieno[3,2-c]pyridin-6-ol (1.26 g, 7.00 mmol) in acetic acid (30 ml) and an off-white solid precipitated. This mixture was stirred for one hour at room temperature. The solid was collected by filtration, washed with acetic acid, triturated with refluxing MeOH, then refluxing Et$_2$O, and dried in vacuo to give the urea (0.798 g, 51% yield); mp 294°–297° C. (dec); IR (KBr) 1525, 1620 and 2300–3100 cm$^{-1}$; mass spectrum m/z 223 (M+); $^1$H NMR (TFA) δ3.02 (s, 3H, 4-CH$_3$), 7.63 and 7.77 each (d, J=6 Hz, 1H, thiophene-H).

Theor. C$_9$H$_9$N$_3$O$_2$S: C, 48.42; H, 4.06; N, 18.82. Found: C, 48.39; H, 4.31; N, 18.38.

EXAMPLE 34

6-Hydroxy-7-[(2-methoxyphenyl)ureylene]-4-methylthieno[3,2-c]pyridine

2-Methoxyphenylisocyanate (0.74 ml, 7.07 mmol) was added to a solution of crude 7-amino-4-methylthieno[3,2-c]pyridin-6-ol (1.00 g, 5.55 mmol) in acetic acid (40 ml) and a solid precipitated immediately. The mixture was stirred for one hour at room temperature, and the off-white solid was collected by filtration, washed with acetic acid, and triturated in Et$_2$O to give the product (450 mg, 25% yield); mp 210°–222° C. (dec); IR (KBr) 1530, 1635, 2500–3600, 3260 and 3340 cm$^{-1}$; mass spectrum m/z 329 (M+); $^1$H NMR (TFA) δ3.00 (s, 3H, 4-CH$_3$), 3.98 (s, 3H, OCH$_3$), 6.87–7.53 (m, 4H, Ar-H), 7.60 and 7.73 each (d, J=5 Hz, 1H, thiophene-H).

Theor. C$_{16}$H$_{15}$N$_3$O$_3$S: C, 58.35; H, 4.58; N, 12.76; S, 9.73. Found: C, 58.01; H, 4.22; N, 12.50; S, 9.66.

When, in the above procedure, 2,3-dimethoxyphenylisocyanate is employed as the starting material, 6-hydroxy-7-[(2,3-dimethoxyphenyl)ureylene]-4-methylthieno[3,2-c]pyridine is obtained.

EXAMPLE 35

6-Hydroxy-7-(4-methoxyphenylureylene)-4-methylthieno[3,2-c]pyridine

4-Methyl-7-nitrothieno[3,2-c]pyridin-6-ol (2.85 g, 13.6 mmol) suspended in acetic acid (50 ml) was hydrogenated using 10% Pd/C (280 mg) as catalyst at 40 psi of H$_2$ for 1.5 hours in a Parr apparatus. The catalyst was removed by filtration and p-methoxyphenylisocyanate (2.1 ml, 16.2 mmol) was added to the filtrate. Within 10 minutes, an off-white solid precipitated. The mixture was stirred at room temperature for one hour, and the precipitate was collected by filtration, washed with acetic acid, triturated with acetone, washed with Et$_2$O and air-dried to give the product (2.87 g, 63% yield); mp 277°–279° C.; IR (KBr) 1560, 1640 and 3290 cm$^{-1}$; mass spectrum m/z 329 (M+); $^1$H NMR (TFA) δ3.03 (s, 3H, 4-CH$_3$), 4.03 (s, 3H, COCH$_3$), 7.13 (d, J=9 Hz, 2H, Ar-H), 7.45 (d, J=9 Hz, 2H, Ar-H), 7.62 and 7.77 each (d, J=5 Hz, 1H, thiophene-H).

For C$_{16}$H$_{15}$N$_3$O$_3$S.¼H$_2$O: Theor: C, 57.56; H, 4.67; N, 12.58; S, 9.60. Found: C, 57.69; H, 4.61; N, 12.51; S, 9.65.

EXAMPLE 36

6-Hydroxy-7-[(2,5-dimethoxyphenyl)ureylene]-4-methylthieno[3,2-c]pyridine

A suspension of 4-methyl-7-nitrothieno[3,2-c]pyridin-6-ol (1.8 g, 8.6 mmol) in acetic acid (35 ml) was hydrogenated using 10% Pd/C (140 mg) as a catalyst in a Parr shaker at 40 psi for 1.5 hours. The catalyst was removed by filtration. 2,5-Dimethoxyphenylisocyanate (1.7 g, 9.5 mmol) was added to the filtrate, and a white solid precipitated within minutes. The mixture was stirred at room temperature for two hours, and the solid was collected by filtration, washed with acetic acid, triturated in acetone, then Et$_2$O to give the product (1.10 g, 36% yield) as a colorless solid; mp 228°–230° C.; IR (KBr) 1645 and 1535 cm$^{-1}$; mass spectrum m/z 360 (MH+); $^1$H NMR (TFA) δ3.03 (s, 3H, CH$_3$), 4.02 (s, 6H, OCH$_3$), 6.92–7.22 (m, 2H, Ar-H), 7.53–7.85 (m, 3H, thiophene-H, Ar-H).

Theor. C$_{17}$H$_{17}$N$_3$O$_4$S: C, 56.81; H, 4.77; N, 11.69; S, 8.92. Found: C, 56.87; H, 4.81; N, 11.47; S, 9.20.

EXAMPLE 37

6-Hydroxy-7-[(3,5-dimethoxyphenyl)ureylene]-4-methylthieno[3,2-c]pyridine

A suspension of 4-methyl-7-nitrothieno[3,2-c]pyridin-6-ol (1.8 g, 8.6 mmol) in acetic acid (35 ml) was hydrogenated using 10% Pd/C (140 mg) as a catalyst in a Parr shaker at 40 psi for 1.5 hours. The catalyst was removed by filtration. 3,5-Dimethoxyphenylisocyanate (1.7 g, 9.5 mmol) was added to the filtrate, and a white solid precipitated within minutes. The reaction mixture was stirred at room temperature for two hours, and the solid was collected by filtration, washed with acetic acid, triturated in acetone, then Et$_2$O to give the product (1.0 g, 33% yield) as an off-white solid; mp 235°–237° C.; IR (KBr) 1650, 1620 and 1550 cm$^{-1}$; mass spectrum m/z 360 (MH+); $^1$H NMR (TFA) δ 3.07 (s, 3H, CH$_3$), 4.02 (s, 6H, OCH$_3$), 6.68 (b.s., 1H, Ar-H), 6.88 (b.s., 2H, Ar-H), 7.65 and 7.78 each (d, J=6 Hz, 1H, thiophene-H).

Theor. $C_{17}H_{17}N_3O_4S$: C, 56.81; H, 4.77; N, 11.69; S, 8.92. Found: C, 56.74; H, 4.82; N, 11.57; S, 9.20.

EXAMPLE 38

6-Acetoxy-4-methylthieno[3,2-c]pyridine

A solution of 4-methylthieno[3,2-c]pyridin-6-ol (1.35 g, 8.17 mmol) and concentrated sulfuric acid (2 drops) in acetic anhydride (10 ml) was stirred for 16 hours at room temperature. The reaction mixture was poured into ice water (50 ml), neutralized with solid $NaHCO_3$, extracted with $CH_2Cl_2$ (2×50 ml) and the organic layers were washed with saturated aqueous $NaHCO_3$ and dried over $MgSO_4$. The solvent was removed in vacuo, and the resultant oil crystallized slowly over several days. The solid was triturated in hexanes and collected by filtration to give the product (0.49 g, 29% yield); mp 38°–40° C.; IR (KBr) 1765 cm$^{-1}$; mass spectrum m/z 208 (MH+); $^1$H NMR (CDCl$_3$) δ 2.37 (s, 3H, COCH$_3$), 2.80 (s, 3H, CH$_3$), 7.42 (s, 3H, thiophene-H, Ar-H).

Theor. $C_{10}H_9NO_2S$: C, 57.95; H, 4.37; N, 6.76; S, 15.47. Found: C, 58.12; H, 4.39; N, 6.75; S, 15.37.

Additional thieno[3,2-c]pyridine derivatives having different $R_2$, $R_3$ or $R_4$ substituents are prepared in an analogous manner to the thieno[2,3-c]pyridine derivatives previously described.

EXAMPLE 39

2,5-Dimethyl-3-thiophene acetic acid

A mixture of 2,5-dimethyl-3-acetylthiophene (10.0 g, 64.8 mmol), sulfur (3.35 g, 0.109 mol) and morpholine (13 ml, 0.149 mol) was heated to reflux for 16 hours. The mixture was poured into 1N HCl (100 ml), and the product was extracted into $CH_2Cl_2$ (2×100 ml), washed with 1N HCl (1×100 ml), and dried over $MgSO_4$. The solvent was removed in vacuo to give an oil (17 g) which was purified by flash chromatography on silica gel 60 (300 g) eluted with 15% EtOAc in hexanes to give a thioamide derivative (11.5 g, 70% yield) as a yellow solid; mp 82°–84° C.; IR (KBr) 1480 and 1435 cm$^{-1}$; mass spectrum m/z 255 (M+); $^1$H NMR (CDCl$_3$) δ 2.30 (s, 3H, CH$_3$), 2.37 (s, 3H, CH$_3$), 3.32–3.85 (m, 6H, OCH$_2$, NCH$_2$), 4.08 (s, 2H, CH$_2$CSN), 4.25–4.45 (m, 2H, NCH$_2$), 6.55 (s, 1H, thiophene-H).

Theor. $C_{12}H_{17}NOS_2$: C, 56.43; H, 6.71; N, 5.48; S, 25.11. Found: C, 56.75; H, 6.85; N, 5.27; S, 25.11.

A solution of the above thioamide (79 g, 0.309 mol) and 50% NaOH in H$_2$O (150 ml) in MeOH (500 ml) was heated to reflux for five hours. The reaction mixture was concentrated in vacuo, diluted to 500 ml with H$_2$O, and acidified with concentrated HCl with cooling to give a yellow precipitate which was collected by filtration, washed with H$_2$O and air-dried to give the product (34.4 g, 65% yield) as a yellow solid; mp 62°–65° C. (lit. mp 69°–70° C.). This was used in the following step without further purification. IR (KBr) 1705 cm$^{-1}$; mass spectrum m/z 170 (M+); $^1$H NMR (CDCl$_3$) δ 2.31 (s, 3H, CH$_3$), 2.38 (s, 3H, CH$_3$), 3.46 (s, 2H, CH$_2$CO$_2$), 6.53 (s, 1H, thiophene-H), 11.08 (b.s., 1H, exchanges with D$_2$O, CO$_2$H).

Theor. $C_8H_{10}O_2S$: C, 56.45; H, 5.92; S, 18.84. Found: C, 56.28; H, 5.98; S, 19.09.

Methyl 2,5-dimethyl-3-thiophene acetate

A solution of 2,5-dimethyl-3-thiophene acetic acid (34 g, 0.200 mol) and concentrated sulfuric acid (1.0 ml) in MeOH (500 ml) was stirred at room temperature for 16 hours. The mixture was concentrated in vacuo, diluted to 500 ml with H$_2$O, and neutralized with solid NaHCO$_3$. The product was extracted with Et$_2$O (2×200 ml), the organic layer was washed with H$_2$O (1×100 ml), dried over MgSO$_4$, and treated with activated charcoal. The solvent was removed in vacuo to give the product (33.2 g, 90% yield) as an oil; IR (neat) 1750 cm$^{-1}$; mass spectrum m/z 184 (M+); $^1$H NMR (CDCl$_3$) δ 2.32 (s, 3H, thiophene-CH$_3$), 2.38 (s, 3H, thiophene-CH$_3$), 3.45 (s, 2H, CH$_2$CO$_2$), 3.67 (s, 3H, CO$_2$CH$_3$), 6.53 (s, 1H, thiophene-H).

Theor. $C_9H_{12}O_2S$: C, 58.67; H, 6.56; S, 17.40. Found: C, 58.77; H, 6.65; S, 17.29.

Methyl 2,5-dimethyl-4-acetyl-3-thiophene acetate

A solution of methyl 2,5-dimethyl-3-thiophene acetate (33.2 g, 0.18 mol) in CH$_2$Cl$_2$ (150 ml) was added to a solution of acetylchloride (15.5 ml, 0.216 mol) and tin (IV) chloride (23.2 ml, 0.198 mol) in CH$_2$Cl$_2$ (200 ml) at 0°–5° C. over a 15 minute period. The solution became a deep red color and was stirred at 0°–5° C. for two hours. H$_2$O (200 ml) was added to the mixture, and the organic layer was separated, washed with saturated aqueous NaHCO$_3$ (1×100 ml), dried over MgSO$_4$, and treated with activated charcoal. The solvent was removed in vacuo to give the product (40.2 g, 97% yield) as an oil with crystallized slowly on standing; mp 68°–71° C.; IR (KBr) 1745 and 1650 cm$^{-1}$; mass spectrum m/z 226 (M+); $^1$H NMR (CDCl$_3$) δ 2.30 (s, 3H, thiophene-CH$_3$), 2.47 (s, 3H, COCH$_3$), 2.60 (s, 3H, thiophene-CH$_3$), 3.67 (s, 5H, CH$_2$CO$_2$CH$_3$).

Theor. $C_{11}H_{14}O_3S$: C, 58.38; H, 6.24; S, 14.17. Found: C, 58.35; H, 6.02; S, 14.04.

2,3,7-Trimethylthieno[3,4-c]pyridin-5-ol (a) A suspension of methyl 2,5-dimethyl-4-acetyl-3-thiophene acetate (20.0 g, 88.4 mmol) in concentrated NH$_4$OH (250 ml) was stirred at room temperature for five days. A solid was collected by filtration and washed with H$_2$O to give 1,3,7-trimethylthieno[3,4-c]pyridin-5ol (2.4 g, 14% yield) as a solid; mp 226°–230° C. (dec); IR (KBr) 1640 cm$^{-1}$; mass spectrum m/z 194 (MH+); $^1$H NMR (TFA) δ 2.67 (s, 3H, 3-CH$_3$), 3.10 (s, 3H, 2 or 7-CH$_3$), 3.20 (s, 3H, 2- or 7-CH$_3$), 6.90 (s, 1H, 6-H).

(b) The aqueous filtrate from (a) was diluted to 200 ml with H$_2$O and extracted with CH$_2$Cl$_2$ (3×200 ml). The combined organic phase was dried over MgSO$_4$ and concentrated to 200 ml. Hexanes (100 ml) were added and the solution was cooled in an ice bath. 2,5-Dimethyl-4-acetyl-3-thiopheneacetamide (5.1 g, 27% yield) crystallized as a colorless solid; mp 123°–125° C.; IR (KBr) 3410 and 1660 cm$^{-1}$; mass spectrum m/z 212 (MH+); $^1$H NMR (CDCl$_3$) δ 2.38 (s, 3H, thiophene-CH$_3$), 2.52 (s, 3H, COCH$_3$), 2.60 (s, 3H, thiophene-CH$_3$), 3.48 (s, 2H, CH$_2$CON), 5.60 (b.s., 1H, NH), 6.75 (b.s., 1H, NH).

Theor. $C_{10}H_{13}NO_2S$: C, 56.84; H, 6.20; N, 6.63; S, 15.18. Found: C, 56.61; H, 6.34; N, 6.58; S, 15.12.

A solution of 2,5-dimethyl-4-acetyl-3-thiopheneacetamide (2.4 g, 11.4 mol) in TFA (25 ml) was stirred at room temperature for 16 hours. The solvent was removed in vacuo. The gummy residue was treated with H$_2$O (50 ml) and neutralized with solid NaHCO$_3$. The brown solid was collected by filtration, washed with H$_2$O and air-dried to give the product (2.1 g, 94% yield). This material was identical in all respects to that described in (a) above.

EXAMPLE 40

5-Acetoxy-2,3,7-trimethylthieno[3,4-c]pyridine

A solution of 2,3,7-trimethylthieno[3,4-c]pyridin-5-ol (5.7 g, 29.5 mmol) and concentrated sulfuric acid (0.2 ml) in acetic anhydride (55 ml) was stirred at room temperature for 16 hours. The solvent was removed in vacuo, and the residue was treated with a saturated aqueous NaHCO$_3$. The product was extracted into CH$_2$Cl$_2$ (2×100 ml), washed with saturated aqueous NaHCO$_3$ (1×100 ml), and dried over MgSO$_4$. The solvent was removed in vacuo, and the residue was purified by flash chromatography on silica gel 60 (100 g) eluted with 1% MeOH in CH$_2$Cl$_2$ to give the product (1.25 g, 18% yield); mp 137°-140° C.; IR (KBr) 1755 and 1590 cm$^{-1}$; mass spectrum m/z 236 (MH+); $^1$H NMR (CDCl$_3$) δ 2.33 (s, 3H, COCH$_3$), 2.57 (s, 3H, 3-CH$_3$), 2.83 (s, 3H, 7-CH$_3$), 2.90 (s, 3H, 2-CH$_3$), 6.76 (s, 1H, 6-H).

Theor. C$_{12}$H$_{13}$NO$_2$S: C, 61.25; H, 5.56; N, 5.95. Found: C, 61.19; H, 5.72; N, 5.95.

Additional thieno[3,4-c]pyridine derivatives having different R$_2$, R$_3$ or R$_4$ substituents are prepared in an analogous manner to the thieno[2,3-c]pyridine or thieno[3,2-c]pyridine derivatives previously described.

EXAMPLE 41

Cardiotonic Activity

The cardiotonic activity of the compounds was tested in accordance with Alousi, A. A., et al, *J. Cir. Res.* 45, 666 (1979). Basically, adult mongrel dogs were anesthetized with sodium pentobarbital and artifically respired. Arterial pressure was recorded via a femoral artery and the pressure pulse used to trigger a cardiotachometer for heart rate. Left ventricular pressure was measured with a Millar catheter and dP/dt was derived. Cardiac output was determined by measuring ascending aortic blood flow with an electromagnetic flow probe and myocardial contractile force was measured with a Walton Brodie strain gauge sutured to the right ventricle. Lead II EKG was also recorded. A standard dose of dopamine or dobutamine was administered to assess myocardial responsiveness. Test compounds were administered by i.v. infusion or bolus administration and the effects on cardiovascular parameters were determined. Dose-related effects of the test compound on BP, HR, dP/dt max., C.F. and C.O. were compared to pretreatment control values and expressed as a percent change. The results are shown in Table I.

TABLE I

Cardiotonic Effects of Representative Thienopyridine Derivatives in Anesthetized Dog

| Compound (Example) | Dose[1] | CF[2] | DP/DT[3] | HR[4] | MABP[5] |
|---|---|---|---|---|---|
| 1 | 1.87 | 62 | 30 | +8 | −7 |
| 2 | 1.87 | 207 | 58 | +17 | −29 |
| 3 | 1.87 | 92 | 119 | +40 | 37 |
| 4 | 1.87 | 96 | 62 | +19 | −34 |
| 5 | 1.87 | 130 | 73 | +52 | −49 |
| 6 | 1.87 | 20 | 18 | +6 | 3 |
| 7 | 1.87 | 7 | 13 | −20 | 14 |
| 8 | 1.87 | 4 | 8 | +3 | 4 |
| 9 | 1.87 | 5 | 5 | +2 | 0 |
| 17 | 1.87 | 49 | 29 | +4 | 10 |
| 18 | 1.87 | 11 | 45 | −9 | 28 |
| 21 | 1.87 | 9 | 14 | +9 | 0 |
| 22 | 1.87 | 62 | 18 | +4 | −1 |
| 24 | 1.87 | 12 | 14 | +4 | −7 |
| 25 | 1.87 | 71 | 24 | +10 | −19 |
| 26 | .875 | 184 | 164 | +40 | −17 |
| 27 | .875 | 77 | 78 | 0 | 1 |
| 28 | 1.87 | 80 | 33 | +11 | −13 |
| 30 | .875 | 88 | 83 | +16 | −32 |
| 31 | 1.87 | 8 | 8 | 0 | −1 |
| 33 | 1.87 | 20 | 17 | +3 | 1 |
| 38 | 1.87 | 61 | 62 | +20 | −3 |

[1]dose in mg/kg
[2]percent increase in cardiac force
[3]percent increase in dp/dt
[4]percent change in heart rate
[5]percent change in mean arterial blood pressure

EXAMPLE 42

Renal Vasodilatory Activity

The renal vasodilatory activity of the compounds was tested as follows. Adult mongrel dogs were anesthetized and surgically prepared for electromagnetic measurement of renal artery blood flow. A carotid artery was cannulated for measuring arterial blood pressure and drugs were administered intravenously or intra-arterially (renal artery). Heart rate (HR) was monitored by a cardiotachometer. Renal vascular resistance (RVR) was calculated as the ratio of mean arterial blood pressure/renal artery blood flow. Dopamine was infused intravenously at 3 μg/kg/min for ten minutes (2 ml/min) to determine responsiveness of each dog to renal dopamine receptor stimulation. Cumulative dose-response data was obtained by infusing the test drug at progressively increasing (usually three-fold) infusion rates, each dose being infused for five minutes. The maximum precent increase from pre-drug control in renal artery blood flow (RBF) or decrease in renal vascular resistance (RVR) was quantitated for each infusion dose. The results are shown in Table II.

TABLE II

Renal Vasodilatory Effects of Representative Thienopyridine Derivatives in Anesthetized Dog

| Compound (Example) | Dose[1] | RBF[2] | RVR[3] | MAP[4] | HR[5] |
|---|---|---|---|---|---|
| 1 | 6.20 | +9 | −18 | −10 | +14 |
| 4 | 6.20 | −19 | −30 | −17 | +22 |
| 6 | 6.20 | +15 | −15 | −2 | +13 |
| 9 | 6.20 | +26 | −20 | +1 | +10 |
| 10 | 6.20 | +5 | +2 | +8 | +3 |
| 11 | 6.20 | +5 | −10 | −5 | +6 |
| 21 | 6.20 | +31 | −19 | +4 | +14 |
| 22 | 6.20 | +56 | −35 | 0 | +2 |
| 28 | 6.20 | +8 | −22 | −17 | +26 |
| 30 | 6.20 | +39 | −48 | −29 | +25 |
| 31 | 6.20 | +14 | −10 | +1 | −7 |
| 34 | 6.20 | +25 | −15 | +5 | +10 |
| * | 6.20 | +18 | −13 | +1 | +3 |
| ** | 6.20 | +83 | −46 | −4 | −6 |

[1]dose in mg/kg
[2]percent increase in renal blood flow
[3]percent decrease in renal vascular resistance
[4]percent change in mean arterial blood pressure
[5]percent change in heart rate
*4-carboxyethylcarbamoyl-5-hydroxy-7-methylthieno[2,3-c]pyridine
**6-hydroxy-7-[(2,3-dimethoxyphenyl)ureylene]-4-methylthieno[3,2-c]pyridine

What is claimed is:
1. A compound of the formula

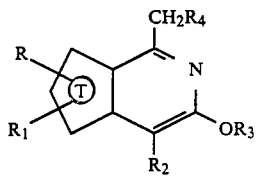

where

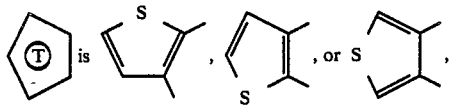 is

R and R₁ are the same or different and are hydrogen or methyl, $R_2$ is hydrogen, Cl, Br, I, $NO_2$, $NH_2$, $C_1$–$C_6$ alkyl, —$CO_2R_5$, —$NHCONHR_6$, —$NHCO_2R_5$ or —$NHCOR_7$, $R_3$ is hydrogen, $COR_8$ or —$(CH_2)_nN(CH_3)_2$, $R_4$ is hydrogen, Br, —$N(R_5)_2$ or

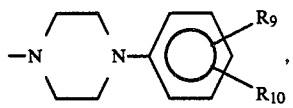

$R_5$ is $C_1$–$C_3$ alkyl, $R_6$ is hydrogen, $C_1$–$C_6$ alkyl or

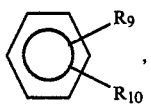

$R_7$ is $C_1$–$C_6$ alkyl or

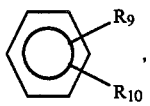

$R_8$ is $C_1$–$C_4$ alkyl or

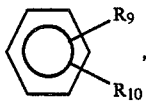

$R_9$ and $R_{10}$ are the same or different and are hydrogen, $C_1$–$C_3$ alkyl, —$OCH_3$ or halogen, and n is 2–5, provided that $R_2$ is not hydrogen when R and $R_1$ are methyl.

2. A compound of claim 1 wherein $R_3$ is hydrogen.

3. A compound of claim 1 wherein $R_3$ is $COR_8$ where $R_8$ is $C_1$–$C_4$ alkyl.

4. A compound of claim 1 wherein $R_3$ is —$(CH_2)_nN(CH_3)_2$.

5. A compound of claim 1 wherein $R_2$ is —$NHCONHR_6$.

6. A compound of claim 1 wherein $R_2$ is —$NHCO_2R_5$ or $NHCOR_7$.

7. A compound of claim 1 wherein $R_2$ is hydrogen, Cl, Br, $NO_2$, $NH_2$, $C_1$–$C_6$ alkyl or —$CO_2R_5$.

8. A compound of claim 1 selected from the group consisting of 7-methylthieno[2,3-c]pyridin-5-ol, 4-ethyl-7-methylthieno[2,3-c]pyridin-5-ol, 4-carbomethoxy-7-methylthieno[2,3-c]pyridin-5-ol, 4-bromo-7-methylthieno[2,3-c]pyridin-5-ol, 4-chloro-7-methylthieno[2,3-c]pyridin-5-ol, 7-methyl-4-nitrothieno[2,3-c]pyridin-5-ol, 4-amino-7-methylthieno[2,3-c]pyridin-5-ol, 4-acetamido-7-methylthieno[2,3-c]pyridin-5-ol, 4-ethyl-7-methyl-5-[3-(N,N-dimethylamino)propoxy]thieno[2,3-c]pyridine, 4-ethyl-7-methyl-5-[2-(N,N-dimethylamino)ethoxy]thieno[2,3-c]pyridine, 7-bromomethyl-4-ethyl-5-hydroxythieno[2,3-c]pyridine, 4-ethyl-7-[[4-(2-methoxyphenyl)piperazin-1-yl]methyl]thieno[2,3-c]pyridin-5-ol, 4-ethyl-7-[[4-(2-methylphenyl)piperazin-1-yl]methyl]thieno[2,3-c]pyridin-5-ol, 7-bromomethyl-4-bromothieno[2,3-c]pyridin-5-ol, 4-bromo-7-[[4-(2-methoxyphenyl)piperazin-1-yl]methyl]thieno[2,3-c]pyridin:5-ol, 5-acetoxy-7-methylthieno[2,3-c]pyridine, 5-acetoxy-4-bromo-7-methylthieno[2,3-c]pyridine, 5-acetoxy-4-ethyl-7-methylthieno[2,3-c]pyridine, 4-methylthieno[3,2-c]pyridin-6-ol, 7-bromo-4-methylthieno[3,2-c]pyridin-6-ol, 4-methyl-7-nitrothieno[3,2-c]pyridin-6-ol, 7-amino-4-methylthieno[3,2-c]pyridin-6-ol and 6-acetoxy-4-methylthieno[3,2-c]pyridine.

9. A compound of claim 1 selected from the group consisting of 5-hydroxy-7-methyl-4-ureidothieno[2,3-c]pyridine, 5-hydroxy-4-(2-methoxyphenylureylene)-7-methylthieno[2,3-c]pyridine, 4-[(3-chlorophenyl)ureylene]-5-hydroxy-7-methylthieno[2,3-c]pyridine, 4-[(4-chlorophenyl)ureylene]-5-hydroxy-7-methylthieno[2,3-c]pyridine, 5-hydroxy-4-[(3-methoxyphenyl)ureylene]-7-methylthieno[2,3-c]pyridine, 5-hydroxy-4-[(4-methoxyphenyl)ureylene]-7-methylthieno[2,3-c]pyridine, 5-hydroxy-4-[(2,4-dimethoxyphenyl)ureylene]-7-methylthieno[2,3-c]pyridine, 5-hydroxy-4-[(3,5-dimethoxyphenyl)ureylene]-7-methylthieno[2,3-c]pyridine, 5-hydroxy-4-[(2,5-dimethoxyphenyl)ureylene]-7-methylthieno[2,3-c]pyridine, 6-hydroxy-4-methyl-7-ureidothiene[3,2-c]pyridine, 6-hydroxy-7-[(2-methoxyphenyl)ureylene]-4-methylthieno[3,2-c]pyridine, 6-hydroxy-7-(4-methoxyphenylureylene)-4-methylthieno[3,2-c]pyridine, 6-hydroxy-7-[(2,5-dimethoxyphenyl)ureylene]-4-methylthieno[3,2-c]pyridine, and 6-hydroxy-7-[(3,5-dimethoxyphenyl)ureylene]-4-methylthieno[3,2-c]pyridine.

* * * * *